US012721889B2

(12) United States Patent
Steffek et al.

(10) Patent No.: US 12,721,889 B2

(45) **Date of Patent: *Sep. 1, 2026**

(54) IMMUNE PRIMING TO ACCELERATE/ENHANCE IMMUNE RESPONSE THROUGH ADMINISTRATION OF NATURAL IMMUNE MODULATOR

(71) Applicant: Zivo Bioscience, Inc., Bloomfield Hills, MI (US)

(72) Inventors: Amy E. Steffek, Bloomfield Hills, MI (US); Andrew A. Dahl, Bloomfield Hills, MI (US); William P. Pfund, Bloomfield Hills, MI (US)

(73) Assignee: ZIVO BIOSCIENCE, INC., Keego Harbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,286

(22) Filed: Feb. 16, 2024

(65) Prior Publication Data

US 2024/0350623 A1 Oct. 24, 2024

Related U.S. Application Data

(63) Continuation of application No. 17/358,878, filed on Jun. 25, 2021, now abandoned.

(60) Provisional application No. 63/044,841, filed on Jun. 26, 2020.

(51) Int. Cl.

| | |
|---|---|
| ***A23K 20/163*** | (2016.01) |
| ***A23K 10/16*** | (2016.01) |
| ***A23K 50/75*** | (2016.01) |
| ***A61K 31/739*** | (2006.01) |
| ***A61K 35/74*** | (2015.01) |
| ***A61K 39/02*** | (2006.01) |
| ***A61K 39/39*** | (2006.01) |
| ***A61P 33/02*** | (2006.01) |
| *A61K 39/00* | (2006.01) |

(52) U.S. Cl.

CPC .............. *A61K 39/39* (2013.01); *A23K 10/16* (2016.05); *A23K 20/163* (2016.05); *A23K 50/75* (2016.05); *A61K 31/739* (2013.01); *A61K 35/74* (2013.01); *A61K 39/0208* (2013.01); *A61P 33/02* (2018.01); *A61K 2039/552* (2013.01); *A61K 2039/55572* (2013.01)

(58) Field of Classification Search

CPC ...... A23K 10/16; A23K 20/163; A23K 50/75; A61K 39/39; A61K 31/739

See application file for complete search history.

(56) References Cited

U.S. PATENT DOCUMENTS

| | | | | |
|---|---|---|---|---|
| 6,140,365 | A | 10/2000 | Kiy et al. | |
| 6,596,477 | B1 * | 7/2003 | Hone | A61K 31/715 424/234.1 |
| 10,017,727 | B2 | 7/2018 | Soma et al. | |
| 2009/0162344 | A1 * | 6/2009 | Soma | A61P 37/08 435/72 |
| 2014/0194287 | A1 | 7/2014 | Soma | |
| 2015/0181909 | A1 | 7/2015 | Levine et al. | |
| 2018/0333443 | A1 | 11/2018 | Embree et al. | |

FOREIGN PATENT DOCUMENTS

| | | | |
|---|---|---|---|
| EP | 0231537 | B1 | 3/1992 |
| EP | 1082908 | B1 | 8/2009 |
| JP | H04182433 | A | 6/1992 |
| WO | 2017127535 | A1 | 7/2017 |
| WO | 2019125128 | A1 | 6/2019 |
| WO | 2020132318 | A1 | 6/2020 |
| WO | 2020172492 | A2 | 8/2020 |
| WO | 2021231869 | A1 | 11/2021 |

OTHER PUBLICATIONS

Komori et al. "Innate Immunity Activated by Oral Administration of LPSp Is Phylogenetically Preserved and Developed in Broiler Chickens", 2015, Anticancer Research, vol. 35, p. 4461-4466. (Year: 2015).*

Ross, "Ross PM3 Broiler Objectives", 2014, p. 1-12. (Year: 2014).*

Suzuki et al. "Homeostasis as regulated by activated macrophage. VI. Protective effect of LPSw (a lipopolysaccharide from wheat flour) against acute infection by Toxoplasma gondii in mice", May 1992, Chem Pharm Bull vol. 40 Issue 5, p. 1266-1267, Abstract only. (Year: 1992).*

Masoud, "Novel adjuvants derived from attenuated lipopolysaccharides and lipid as of purple non-sulfur photosynthetic bacteria", Jun. 6, 2019, Vaccine, vol. 37, Issue 26, pp. 3472-3477 (Year: 2019).*

Benjamin A.L. et al; "Neonatal lipopolysaccharide exposure does not diminish the innate immune response to a subsequent lipopolysaccharide challenge in Holstein bull calves"; Journal of Dairy Science; vol. 99, No. 7; pp. 5750-5763; XP029602013, ISSN: 0022-0302; DOI: 10.3168/JDS.2015-10804.

(Continued)

*Primary Examiner* — Samira J Jean-Louis
*Assistant Examiner* — Amelia Nicole Dickens

(57) ABSTRACT

A method and compound for altering the status of both innate and adaptive immune pathways in both animals and humans are disclosed. The status alteration results in the immune response being primed whereby an accelerated and more robust response is generated when the animal or human is challenged by pathogens that lead to a wide range of disease states. The disclosed method utilizes a compound derived from a lipopolysaccharide (LPS) of gram-negative bacteria. The compound itself is a natural product with no observed adverse environmental impact. By priming the immune pathways according to the disclosed inventive concept, the severity of various disease states can be reduced, can be resolved more quickly, or can be avoided entirely.

3 Claims, 18 Drawing Sheets
(18 of 18 Drawing Sheet(s) Filed in Color)

(56) References Cited

OTHER PUBLICATIONS

Levine, R., et al.; "Evaluation of the effects of feeding dried algae containing beta-1,3-glucan on broilers challenged with Eimeria"; Poultry Science, vol. 97, No. 10; Oct. 1, 2018; pp. 3494-3500, XP055722067; ISSN: 0032-5791; DOI: 10.3382/ps/pey227.

Anonymous; "Zivo Bioscience Announces Impressive Long-Term Benefits for Broiler Poultry Nutrition and Growth Promotion"; Mar. 18, 2020; XP093134996.

Vijayan, V et al; Human and murine macrophages exhibit differential metabolic responses tolipopolysaccharide—A divergent role for glycolysis, Redoc Bioligy, Feb. 20, 2019; vol. 22, No. 101147, pp. 1-9, entire document.

International Search Report, Written Opinion and Cited References, Oct. 21, 2021.

European Search Report, Written Opinion and Cited References, Jul. 5, 2024.

Benjamin, A.L. et al., 'Neonatal lipopolysaccharide exposure does not diminish the innate immune response to a subsequent lipopolysaccharide challenge in Holstein bull calves', Journal of Dairy Science, vol. 99, Issue 7, pp. 5750-5763., Jul. 2016.

Levine R, Horst G, Tonda R, Lumpkins B, Mathis G. Evaluation of the effects of feeding dried algae containing beta-1,3-glucan on broilers challenged with Eimeria. Poult Sci. Oct. 1, 2018;97(10):3494-3500. doi: 10.3382/ps/pey227.

* cited by examiner

IMMUNE PRIMING TO ACCELERATE/ENHANCE IMMUNE RESPONSE THROUGH ADMINISTRATION OF NATURAL IMMUNE MODULATOR

CROSS REFERENCE TO RELATED APPLICATIONS

This application is a continuation of U.S. Non-Provisional patent application Ser. No. 17/358,878, entitled "Immune Priming to Accelerate/Enhance Immune Response Through Administration of Natural Immune Modulator," filed Jun. 25, 2021, which was a U.S. Non-provisional Patent Application of U.S. Provisional Patent Application No. 63/044,841, entitled "Immune Priming to Accelerate/Enhance Immune Response Through Administration of Natural Immune Modulator," filed Jun. 26, 2020, both of which are herein incorporated by reference in their entireties for all purposes.

TECHNICAL FIELD

The present disclosed inventive concept relates to immune systems in animals and humans. More particularly, the disclosed inventive concept relates to a method and treatment using a compound that alters the status of both innate and adaptive immune pathways in both animals and humans. The status alteration results in the immune response being primed whereby an accelerated and more robust response is generated when the animal or human is challenged by pathogens that lead to a wide range of disease states.

BACKGROUND OF THE INVENTION

Substantial economic losses in many animal industries, including the poultry industry, are most often the result of disease. Diseases in flocks often result in reduced productivity or compromises in the safety or quality of the final product introduced into the food supply. Prevention and treatment of poultry disease adds significantly to poultry production costs. Some estimates place total losses due to poultry disease at more than 10% of all production costs.

Of the diseases known to strike poultry flocks, the most common are enteric diseases which include coccidiosis, a disease caused by a parasite, the coccidian protozoa. Annual economic losses due to coccidiosis alone are estimated to exceed $3 billion per year and these costs are expected to increase due to a variety of reasons.

Firstly, coccidiosis prevention today is accomplished primarily through the use of vaccines to forestall pathogenic infection. A one-time administration of a vaccine is given very early in broiler life and, specifically, on the day of hatch. While this approach has shown some benefit, vaccines are known to suffer from very poor effectiveness in controlling the disease over time. Experimentation has shown that a vaccine used in conjunction with a supplement such as a probiotic may improve outcome, but this approach adds to production cost.

Secondly, coccidiosis treatment today is accomplished conventionally through the use of antibiotics and ionophores, both of which are costly. The pre-emptive use of antibiotics and ionophores is under pressure across the globe for a number of reasons, including consumer resistance, regulatory scrutiny and environmental considerations. Recently, the European Union banned sub-therapeutic doses of certain antibiotics for use as feed additives. Other synthetic treatment compounds and chemical agents are known and in use, but are not as effective as conventional antibiotics or ionophores.

Thirdly, drug resistance to antibiotics, ionophores, and pathogen-specific treatment compounds is increasing largely due to overuse, thereby significantly compromising the effectiveness of these treatments. Concurrently, there has been no approval of new drugs in any of these categories for many years.

Fourthly, even if current treatments were economical and effective as claimed, these approaches would still be regarded as unsatisfactory because the medication must be included in the animal's feed for the full duration of the grow period to be fully effective. This requirement adds significant cost to feed for the entire grow period.

Accordingly, it is desirable to develop a non-antibiotic based treatment method and/or compound which can limit or eliminate diseases (including but not limited to coccidiosis) by priming immune pathways in the animal, thereby providing an accelerated and more robust response when challenged by pathogens.

SUMMARY OF THE INVENTION

The disclosed inventive concept provides an improved long-term treatment for a broad variety of diseases in both animals and humans. In animals, and particularly in poultry, the treatment method and composition has proven effective against, for example, coccidiosis. The compound is easy to administer and is cost effective. The disclosed method and composition provide both disease prevention and treatment by way of immune priming.

The compound of the disclosed inventive concept is combined with conventional feed for administration to animals, such as poultry. Human application is possible, as well. The feeding regimen changes the status of the innate (early stage) immune pathways as well as the adaptive (later stage) immune pathways whereby the overall immune system is primed. The result of such immune priming is an accelerated and more robust response when challenged by pathogens including, but certainly not limited to, coccidiosis. It is to be understood that the disclosed method and compound are applicable to a wide variety of disease in both animals and humans where immune priming would not only reduce the severity and term of the disease state but may also prevent it entirely.

During the treatment period, the disclosed compound derived from a lipopolysaccharide (LPS) of gram-negative bacteria is administered to the animal by way of poultry feed, drinking water, or both. The composition itself is a natural product and thus has no adverse environmental impact unlike known antibiotic regimens. Thus, the approach of the disclosed inventive concept stands in sharp contrast to known and commonly used disease treatments.

Data indicate that feeding healthy chickens (specifically, broiler chickens) a corn/soy diet supplemented with biomass, the inventive compound of algal culture, improves growth efficiency while simultaneously improving immune response compared to birds fed the same diet without algal culture biomass supplementation. It should be understood that while reference herein is made to a conventional diet of corn and soy, the disclosed compound may also be used to advantage in combination with other forms of conventional animal feed, such as, but not limited to, wheat.

Kinomic analysis of tissues collected from sacrificed birds fed the dietary mixture of the inventive compound and conventional feed suggests that the biomass causes an alteration of signaling in multiple growth-related pathways. These pathways include, but are not limited to, those associated with the vascular endothelial growth factor (VEGF), the mitogen-activated protein kinase (MAPK or MAP kinase), Ak strain transforming (Akt), and the neurotrophic tropomyosin-related kinase (NTRK). Evidence supports the conclusion that this alteration represents the activation of the various pathways.

The disclosed inventive concept has numerous applications in humans and animals including but not limited to: (1) improving the efficacy of vaccines; (2) reducing the amount of vaccine required for protection; (3) functioning as a general booster of immune health as a dietary supplement; and (4) an overall reduction in the need for antibiotics.

DESCRIPTION OF THE DRAWINGS

The patent or application contains at least on drawing executed in color. Copies of this patent or patent application publication with color drawing(s) will be provided by the Office upon request and payment of the necessary fee.

For a more complete understanding of this invention, reference should now be made to the accompanying figures which are described as follows.

DETAILED DESCRIPTION OF THE PREFERRED EMBODIMENT

Figure 1:
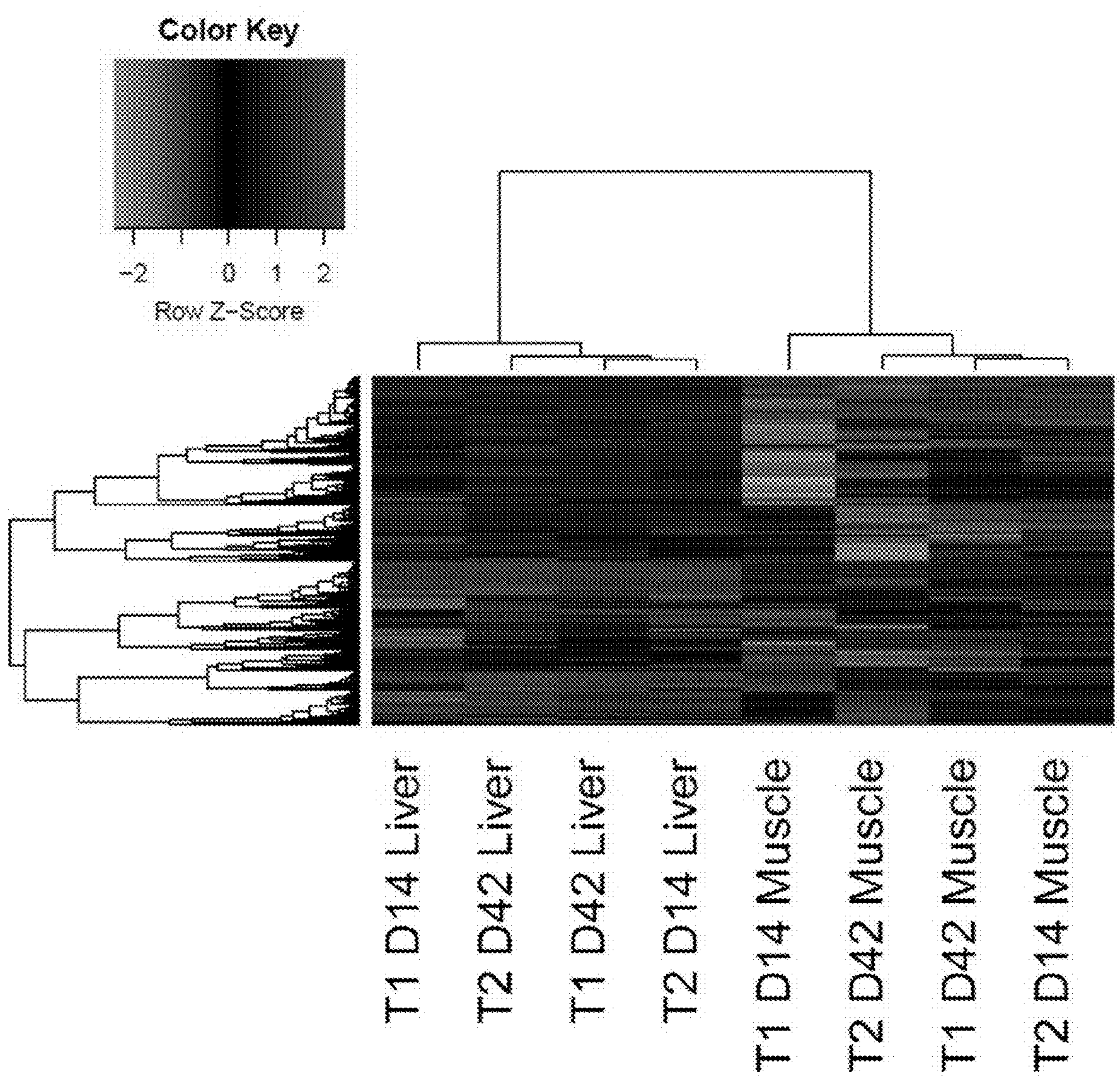
FIG. 1 illustrates a heatmap of liver and muscle tissue kinotypes.

In the following description, various operating parameters and components are described for different constructed embodiments. These specific parameters and components are included as examples and are not meant to be limiting. Unless otherwise noted, all technical and scientific terms used herein are to be accorded their common meanings as would be understood by one having ordinary skill in the art.

The method of the disclosed inventive concept proposes the use of a compound comprising an algal biomass as well as related materials including, for example, algal supernatant, symbiont bacteria, bacterial biomass, and bacterial fermentate. The compound is fed to broiler chickens, as well as other animals, to thereby change the status of innate (early stage) and adaptive (later stage) immune pathways, such that the immune response is primed for an accelerated and more robust response when challenged by pathogens such as, but not limited to, coccidiosis.

The positive effects have been directly demonstrated via kinomic analysis of broiler tissues from birds fed or not fed the compound. Indirect evidence of these same positive effects is provided by coccidiosis challenge studies performed in broilers showing that compound-fed birds exhibited enhanced efficacy of a vaccine for the prevention of coccidiosis. In addition, the broad-spectrum nature of the resulting immune response is indicated by reduced pathogenic bacterial counts (*Salmonella, C. Perfringens, E. coli, Campylobacter*) in the intestines of birds treated with the disclosed compound.

The Compound Used in Treatment

The disclosed method of treatment utilizes an effective compound generally derived from a lipopolysaccharide (LPS) of gram-negative bacteria. By administering the compound early in broiler life, disease prevention and treatment via immune modulation can be accomplished. The effective compound may also be derived from a source other than a lipopolysaccharide.

As used herein, the term "inhibitor" refers to a molecule that reduces or attenuates the activity induced by another molecule. By way of example, a compound that might block the LPS-dependent activation of TLR4 receptors (or possibly TLR2 receptors) present on the surface of immune cells in humans and animals would be regarded as an inhibitor of this particular pathway.

As used herein, the term "algal culture" is defined as an algal organism and bacteria (one or more types) that grow together in a liquid medium. Unless expressly stated otherwise, the term "algal biomass" refers to the algal cells and bacterial cells (with the liquid culture medium removed). The "algal biomass" can be wet material or dried material.

Unless expressly stated otherwise, the term "algal supernatant" is defined as the culture medium in which the algal biomass is grown that contains excreted compounds from the algal biomass. Algal supernatant is obtained by growing algal biomass in culture medium for an appropriate length of time and then removing the algal and bacterial cells by filtration and/or centrifugation.

It is known that bacteria that are part of the *Variovorax* genus and the *Rhodobacter* genus are metabolically versatile. *Variovorax* is a gram-negative aerobic bacterium that can grow under a variety of conditions. It is part of the subclass Proteobacteria and is capable of metabolically utilizing several natural compounds generated by plants. *Rhodobacter* can grow under a broad variety of conditions, including both photosynthesis and chemosynthesis. Growth can also be achieved under both anaerobic and aerobic conditions. *Rhodobacter sphaeroides* represent a gram-negative facultative bacterium and is a member of the $\alpha$-3 subdivision of the Proteobacteria.

Embodiments of the compound used in the prevention and treatment of disease as set forth herein include one or more LPS/Lipid A compounds produced by gram-negative bacterial strains for use as selective inhibitors of the TLR4 (or possibly TLR2) signaling pathway. The disclosed inventive concept involves any combination of three fundamental steps: (1) the gram-negative bacteria produce LPS/Lipid A compounds; (2) the LPS/Lipid compounds modulate TLR4 activity through inhibition; and (3) a downstream effect results in reduced inflammation of the gut via the blockage of TLR4 (or possibly TLR2) signaling thereby aiding in the treatment of coccidiosis.

In an embodiment, the LPS/Lipid A compounds used as selective inhibitors of the TLR4 (or possibly TLR2) signaling pathway are produced from a *Variovorax paradoxus* strain. The *Variovorax paradoxus* strain may be a naturally occurring strain found in an algal biomass and/or algal supernatant products. For example, the algal biomass may comprise the algal species *Klebsormidium flaccidum*. More specifically, the algal biomass culture may comprise the algal strain *Klebsormidium flaccidum*, var. ZIVO.

In another embodiment, the LPS/Lipid A compounds used as selective inhibitors of the TLR4 (or possibly TLR2) signaling pathway are produced from a *Rhodobacter sphaeroides* strain. Extensive studies have been undertaken generally regarding the structure and function of *Rhodobacter sphaeroides*. More focused studies have examined the photosynthetic characteristics of *Rhodobacter sphaeroides*. While it is known that lipopolysaccharides from *Rhodobacter sphaeroides* are effective TLR4 (or possibly TLR2) antagonists in human cells, which prevent TLR4-mediated inflammation by means of blocking LPS/TLR4 (or possibly TLR2) signaling, the inventors had uncovered an LPS compound derived from *Rhodobacter sphaeroides* that proved effective as a coccidiostat in poultry. While initial data suggested inhibition by an LPS-like molecule, it was not until specific testing directed toward *Rhodobacter sphaeroides* revealed the effectiveness of this bacteria in the treatment of disease, such as in the treatment of coccidiosis in poultry. Research further showed that combining a TLR4 inhibitor with an activator of TLR2 (such as LPS from many gram-negative bacteria) provides an anti-coccidiosis effect.

Accordingly, embodiments of the compound used in the treatment of disease according to the present disclosure are directed to one or more LPS/Lipid A compounds produced by a gram-negative bacterial strain of the genus *Variovorax* or the genus *Rhodobacter* for use as selective inhibitors of the TLR4 (or possibly TLR2) signaling pathway. A specific embodiment of the disclosed inventive concept is directed to the use of an LPS/Lipid A compound used as a selective inhibitor of the TLR4 (or possibly TLR2) signaling pathway produced from the *Variovorax paradoxus* strain and the *Rhodobacter sphaeroides* strain.

The LPS/Lipid A compound employed herein may be obtained from the *Variovorax paradoxus* strain or the *Rhodobacter sphaeroides* strain by any suitable method, but in specific embodiments they are extracted using standard multi-step LPS extraction protocols, such as: (1) extracting freeze-dried bacteria with a solution of phenol/guanidine thiocyanate and collecting the water layer for freeze-drying; (2) resolubilizing the freeze-dried fraction in water; (3) ultrafiltration of the solubilized fraction to remove low molecular weight substances and salts; (4) affinity purifying the high-molecular weight fraction using a polymyxin B resin column such as Affi-prep polymyxin matrix material (Bio-Rad), from which an active fraction is eluted with 1% deoxycholate and, optionally; (5) performing additional purification using size-exclusion chromatography.

In some examples, multiple types of LPS extraction protocols are employed to obtain an LPS compound from the bacteria, and extraction procedures may be performed more than once. Once the LPS compound is extracted and purified from the bacteria, the Lipid A fraction may be prepared by acid hydrolysis or other suitable technique.

The one or more LPS/Lipid A compounds derived from gram-negative bacterial strains, such as *Variovorax paradoxus* or *Rhodobacter sphaeroides*, may selectively inhibit the TLR4 (or possibly TLR2) signaling pathway to reduce and/or inhibit inflammatory responses and to improve immune health in a variety of uses and applications. In an embodiment, the LPS/Lipid A compound derived from *Variovorax paradoxus* or *Rhodobacter sphaeroides* may be incorporated within an algal-based feed ingredient to improve gut health of poultry.

The disclosed LPS/Lipid A compound derived from *Variovorax paradoxus* or *Rhodobacter sphaeroides* may be used to improve the health of poultry through a variety of mechanisms. For example, the LPS/Lipid A compound may protect against internal inflammation in poultry by negatively regulating inflammatory mediators via the down-regulation of TLR4 (or possibly TLR2) expression and the inhibition of NF-kappa B activation. In another example, the LPS/Lipid A compound may inhibit the activation of TLR4 (or possibly TLR2) in poultry by interfering with cysteine residue-mediated receptor dimerization. In yet another example, the LPS/Lipid A compound may inhibit the ability of non-infectious and infectious stimuli to interact with TLR4 (or possibly TLR2) and trigger a pro-inflammatory response to improve poultry gut integrity.

The combined batch is preferably provided in an amount of between about 0.5 lbs. composition per ton of finished feed to about 11.0 lbs. composition per ton of finished feed, is more preferably provided in an amount of between about 1.0 lbs. composition per ton of finished feed to about 5.0 lbs. composition per ton of finished feed, and is most preferably provided in an amount of between about 3.0 lbs. composition per ton of finished feed to about 4.0 lbs. composition per ton of finished feed. The ideal suggested and non-limiting ratio is about 3.5 lbs. composition per ton of finished feed.

Treatment Method

A non-limiting example of a method for treating disease is set forth. It is to be understood that while the following method is directed to the treatment of poultry, the disclosed treatment may apply as well to other animals as well as humans. According, the described treatment method is not intended as being solely for use in poultry.

Example

According to the present, non-limiting example, the inventive compound is defined as the algal biomass as set forth above and related materials including algal supernatant and symbiont bacteria. The disclosed treatment compound was mixed with conventional feed to form a "feed mixture" at a fixed ratio at a ratio of 3.5 lbs. compound to one ton of feed. This ratio was maintained throughout the test period. The feed mixture was given to immune-naive birds on Day 1 as part of an ordinary feeding regimen and continued through the study period in an equal ratio. The "treatment compound" was represented by the algal biomass as set forth above and related materials including algal supernatant and symbiont bacteria. All ratios were maintained during the feeding period. The chickens were subjected to normal stress found in a minimum 25% of the US chicken population. This included being raised on built-up litter from previous flocks to replicate the typical stress experienced in the US Poultry Production arena.

Two growth-promoting treatment regimens were administered:

Treatment 1 (T1)=corn-soy diet control

Treatment 2 (T2)=corn-soy diet+algae

The growth-promoting compound according to the present disclosed inventive concept was tested at a research university in a 42-day broiler pen study. Overall, the results showed that after Day 14 of life, birds fed a feed composition including the disclosed inventive compound and a corn/soy mixture demonstrated improved metabolism and improved immune response compared to control animals fed only the corn/soy mixture. An on-going review of small segments of numerous other studies in which healthy birds were fed a composition containing the inventive compound for a limited time before a disease challenge was applied preliminarily suggests positive effects of the inventive compound in healthy animals when combined with convention animal feed.

After completion of the growth period, muscle, liver, small intestine, and ceca tissue were collected from five birds from each of the two diet groups at days 14 (D14) and 42 (D42) post hatch. Tissue samples were removed from chickens and immediately flash frozen in liquid nitrogen to preserve kinase enzymatic activity. Samples were kept on dry ice and stored at −80° C. until the experimental protocol was conducted. Tissue samples were thawed, and a 40 mg section was collected and placed in 2.0 mL homogenizer tubes containing 1.5 mm Zirconium beads and 100 uL of lysis buffer. Samples were homogenized in a Bead Ruptor®.

Homogenized tissue was then incubated on ice for 10 min then spun in a microcentrifuge. Peptide array production was then undertaken generating 771 unique kinase substrate target peptide sequences printed in replicate nine times.

A glass lifter slip was applied to the microarray to sandwich and disperse the applied lysate. Eighty μL of the mixture were applied to the peptide microarray, ensuring that no bubbles were present in the pipette tip or array slide. Slides were incubated for 2 h in a humidity chamber: a sealed container containing a small amount of water (not in contact with the arrays) within an incubator. Arrays were removed from the incubator and humidity chamber and placed in a centrifuge tube containing phosphate-buffered saline. The arrays were submerged in a solution repeatedly until the lifter slip slid off the array. Arrays were then submerged and agitated. This process was then repeated with fresh solution. Arrays were submerged in distilled deionized H2O(ddH2O) and agitated. Array slides were removed from the ddH2O and submerged in phospho-specific fluorescent stain in a dish and placed on a shaker table. The dish was covered to protect the fluorescent stain from light. Arrays were then placed in a new dish and submerged in destaining solution with agitation. The petri dish was covered to protect the stain from light. This process was repeated two times. A final wash was done with ddH2O.

Arrays were then placed in mL centrifuge tubes with a crumpled Kimwipes® in the bottom. The tubes containing the arrays were then centrifuged to remove any moisture from the array. Arrays were scanned using a Tecan® PowerScanner™ microarray scanner at 532 to 560 nm with a 580-nm filter to detect dye fluorescence.

Statistical and Data Analysis

Images were generated and the spot intensity signal was collected as the mean of pixel intensity using local feature background intensity calculation with the default scanner saturation level.

Images were gridded and the spot intensity signal was collected as the mean of pixel intensity using local feature background intensity calculation with the default scanner saturation level. The resultant data were then analyzed by PIIKA2 peptide array analysis software. Briefly, the resulting data points were normalized to eliminate variance due to technical variation, e.g., random variation in staining intensity between arrays or between array blocks within an array. Variance stabilization normalization was performed. It should be noted that as the arrays were printed with triplicate peptide blocks, there were three values for each peptide. Using the normalized data set, comparisons between growth-promoting treatment and control groups were performed, calculating fold change and a significance P-value. The P-value was calculated by conducting a one-sided paired t test between growth-promoting treatment and negative control values for a given peptide. The resultant fold change and significance values were then used to generate optional analysis (including heatmaps, hierarchical clustering, principal component analysis, and pathway analysis).

The four tissues analyzed by chicken-specific kinome peptide arrays (small intestine, liver, muscle, ceca) were run through the analysis pipeline, Platform for Integrated, Intelligent Kinome Analysis 2 (PIIKA2) in two batches, liver and muscle in one and ceca and small intestine (area surrounding the Meckel's diverticulum) in the other. The heatmap of the liver and muscle kinome signal is shown in FIG. 1. Each column in the figure represents the total phosphorylation signal of the tissue from the array. This is referred to as the kinome profile or kinotype of the tissue. The connecting lines at the top of the figure represent the clustering, or relative similarity of kinotypes between each tissue. There is a strong similarity between samples of the same tissue regardless of treatment or age of birds. This is reflected in the two distinct clusters in FIG. 1, one for liver and one for muscle. This similarity is to be expected as muscle and liver are very physiologically and functionally distinct and would be expected to display distinct kinome profiles. Within each tissue cluster, the D14 T1 samples cluster separately from the other groups. This indicates that the effect of the algae addition to the diet was to make the D14 tissue look more similar to D42 tissue overall.

FIG. 1 is a heatmap of liver and muscle tissue kinotypes showing data post PIIKA2 analysis. Each colored line within each column represents a peptide on the array. Red indicates relative increase in phosphorylation, green is relative decrease. General kinotype clustering displays predominantly tissue specific clustering.

When the growth-promoting treatment is compared to the control (T2 vs T1) pairs for each time-matched tissue, the signal is eliminated that was not due to the addition of the algae to the diet. This generates a fold change increase or decrease in phosphorylation relative to control for each peptide (fold change peptide X=T2 peptide X/T1 peptide X). This data was then clustered for relative similarity. It was found that the liver and muscle tissues at D14 were most similar (shown in FIG. 2). This indicates that the algae product is having a similar signaling effect on both tissues at D14 and possibly that effect was strongest at this early time point.

Figure 2:
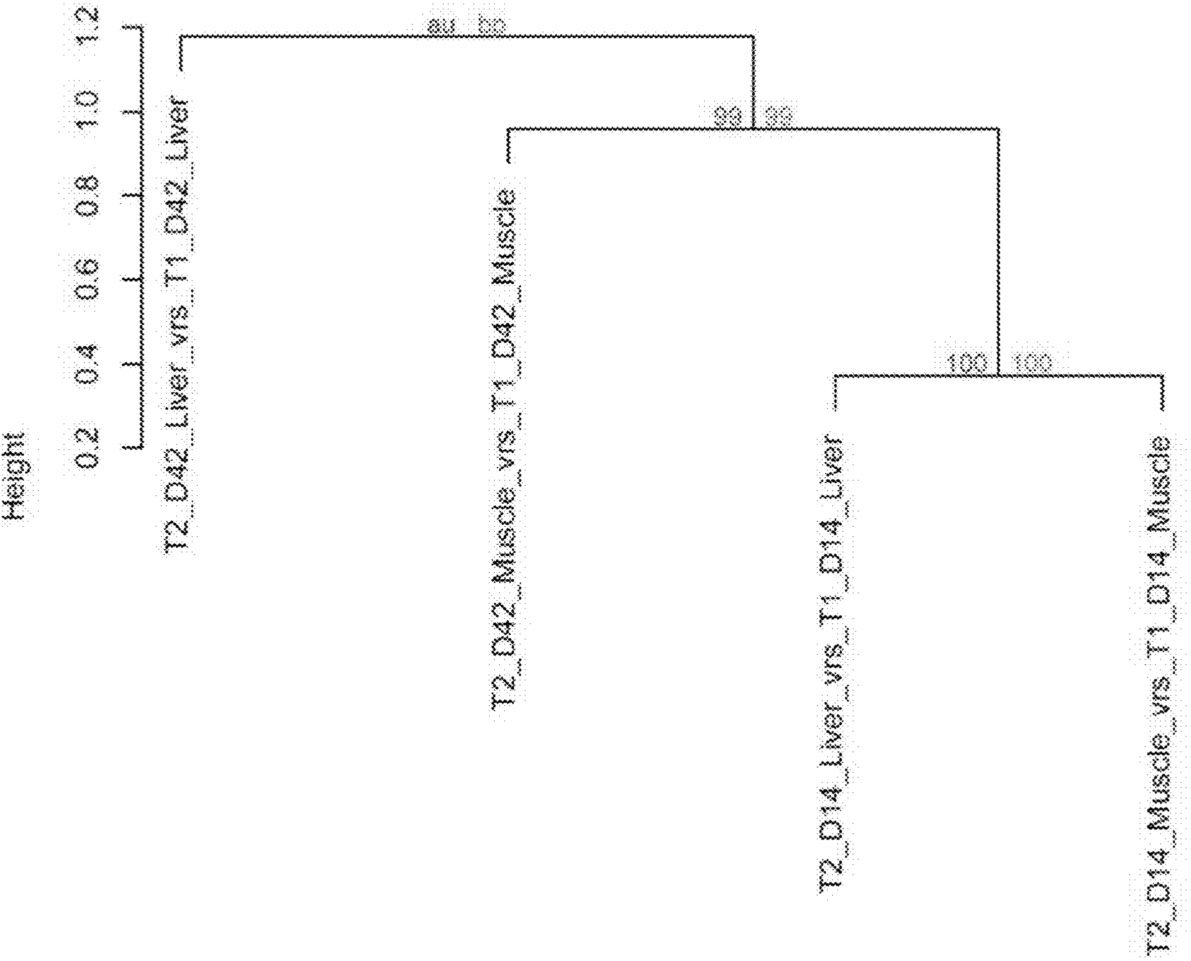
FIG. 2 illustrates a dendrogram of liver and muscle tissue (T2 vs T1)

FIG. 2 is a dendrogram of liver and muscle tissue (T2 vs T1). Clustering the kinotypes following calculation of fold change. By removing the control corn-soy diet and tissue related responses from the kinotypes it may be seen that the augmented diet brings the two tissues into closer alignment based on growth-promoting treatment and age at D14.

When the tissues of the gut are considered, specifically the small intestine (surrounding the Meckel's) and the ceca (shown in FIG. 3), a pattern similar to that of FIG. 1 may be seen. There is a strong similarity between samples of the same tissue regardless of treatment or age of birds. This similarity is to be expected as the small intestine and the ceca are also physiologically and functionally distinct and would be expected to display distinct kinome profiles. However, unlike with the liver and muscle the T1 D14 small intestine and ceca samples cluster together outside of their respective tissue clusters. This indicates that the effect of the algae addition to the diet was to make the D14 tissue look more similar to D42 tissue overall. The clustering pattern is even more striking in FIG. 3 than in FIG. 1 as the T1 D14 tissues actually cluster completely apart from the other samples, though there were significant differences between the two as shown by the length of the lines connecting the two columns.

Figure 3:
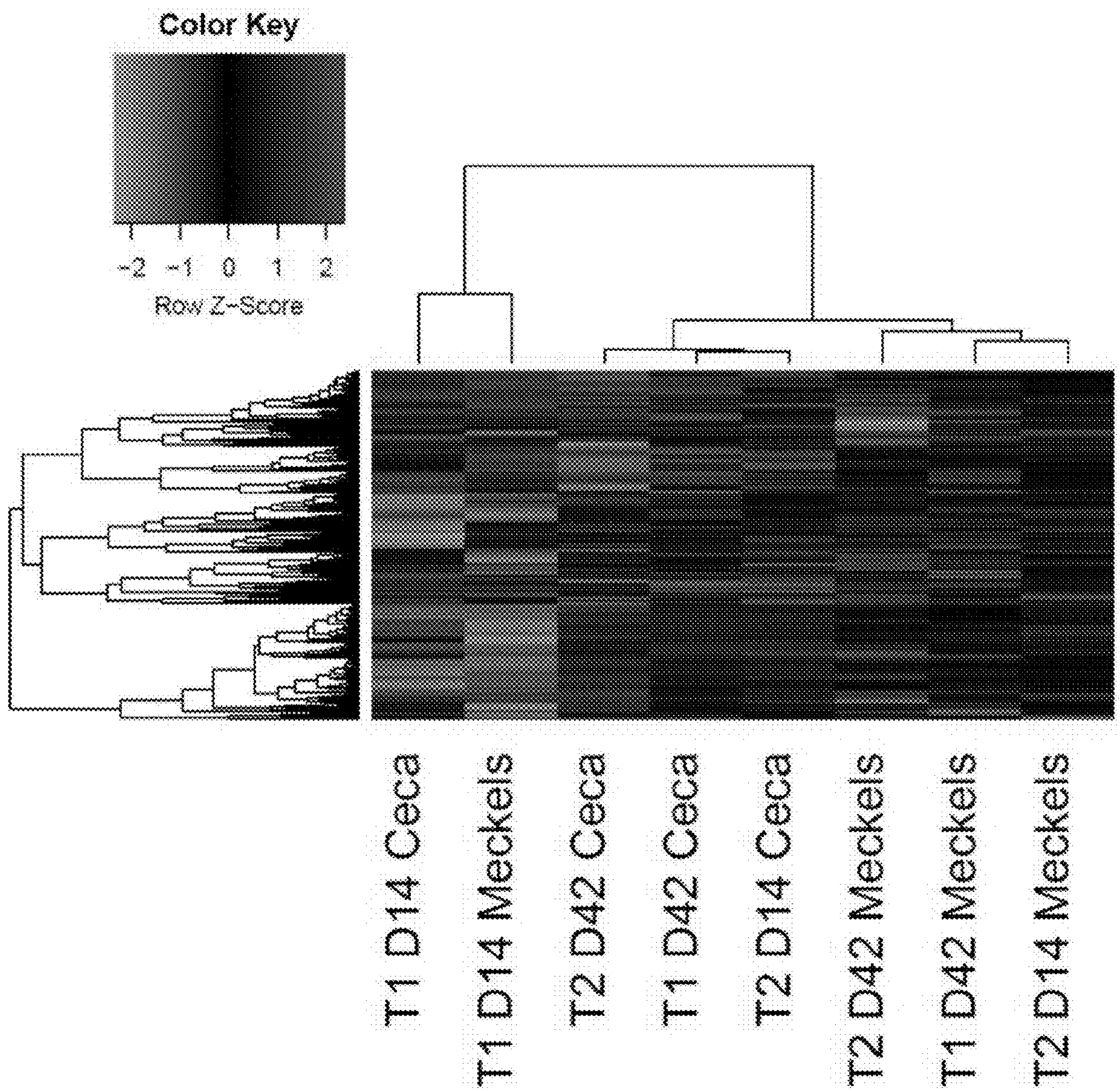
FIG. 3 illustrates a heatmap of small intestine and ceca kinotypes.

FIG. 3 is a heatmap of small intestine and ceca kinotypes showing data post PIIKA2 analysis. Each colored line within each column represents a peptide on the array. Red indicates relative increase in phosphorylation, green is relative decrease. General kinotype clustering shows tissue-based clustering with the exception of D14 T1 groups.

As mentioned above, when the growth-promoting treatment is compared to the control (T2 vs T1) signal that was not due to the addition of the algae to the diet may be eliminated. This data was then clustered for relative similarity. It was found that the small intestine and ceca tissues at D14 were most similar (shown in FIG. 4). This indicates that the algae product is having a similar signaling effect on both tissues at D14 and possibly that effect is strongest at the early time point.

Figure 4:
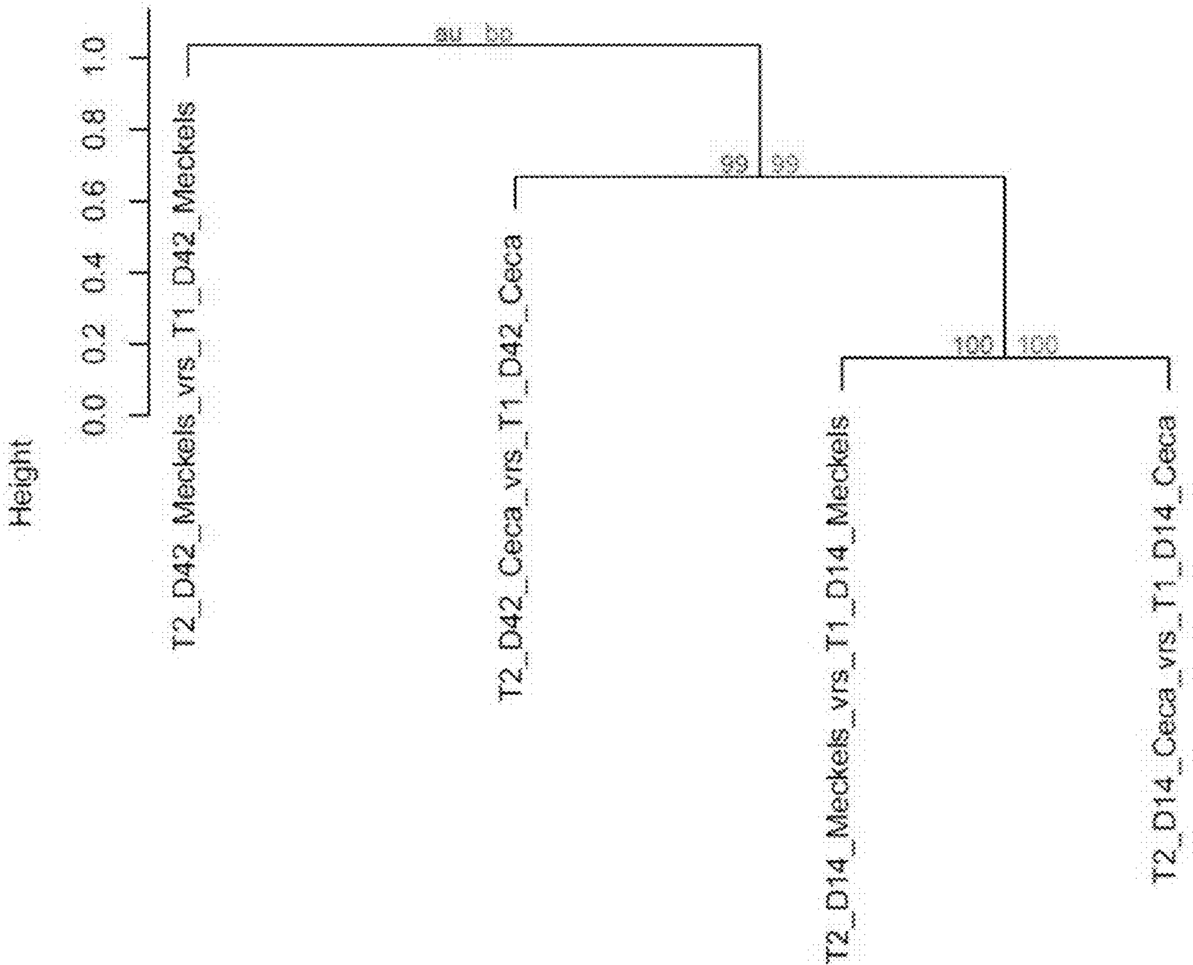
FIG. 4 illustrates a dendrogram of small intestine and ceca tissue (T2 vs T1)

FIG. 4 is a dendrogram of small intestine and ceca tissue (T2 vs T1). This figure demonstrates a clustering the kinotypes following calculation of fold change. By removing the control corn-soy diet and tissue related responses from the kinotypes it can be seen that the augmented diet brings the two tissues into closer alignment based on growth-promoting treatment and age at D14.

Based on the above data from the four tissues, it appears that the strongest impact of the algae supplementation to the diet occurs at D14. This was especially true in the gut tissue as the product appears to make a D14 gut look more like a D42 gut, regardless of if the D42 gut received supplement or not (shown in FIG. 3). When comparing treatment to time matched control, and only considering the effect of the algae, the pattern of signaling changes is consistent between the tissue pairs in the small intestine and ceca, and liver and muscle. FIGS. 2 and 4 show that the D14 samples cluster together, separately from the D42 samples. The above data shows evidence that the algae product was maturing the tissue at D14, causing its kinome profile to appear similar to a mature tissue at D42.

By analyzing what protein changes were occurring at D14 compared to D42, the kinome changes behind this clustering pattern may be understood. The proteins that displayed statistically significant differences between algae treatment and control for each tissue and each time point were input into the STRING database to generate signaling pathways. (The "STRING" database as used herein refers to "Search Tool for the Retrieval of Interacting Genes/Proteins," a biological database and web resource of known and predictable protein-protein interactions taken from several sources including computational prediction methods, public text collections, and experimental data.) This data can then be analyzed to determine changes in biological function resulting from the algae.

In the Following Tables:

"Proteins" references the number of proteins within the pathway differentially phosphorylated on the array, while "Background" is the number of proteins within the pathway, and "FDR" is false discovery rate significance value of the pathway.

"Reactome" refers to an open-source, open access, manually curated and peer-reviewed pathway database used in support of basic and clinical research related to genome analysis and modeling.

"MYD88" refers to the first known downstream component of TLR4 and TLR2 signaling.

"TRIF (TICAM1)-mediated TLR4 signaling" or "Toll-Like Receptor Adaptor Molecule 1" refers to a protein coding gene. The activated TLR4 signaling pathway is related to TICAM1.

"Fc Epsilon Receptor (FCER1)" refers to the high-affinity IgE receptor for the Fc region of immunoglobulin E (IgE). It is also as FcεRI or Fc epsilon RI.

Table 1 A and B shows the top 20 pathways in the small intestine tissue that were changed by the addition of algae to the diet at D14 in Table 1 A) D14 and Table 1B) D42. Highlighted in italics are the pathways that were unique to the specific day.

At D42 with the algae supplement there was an increase in the adaptive immune response (Table 1 B), perhaps indicating a more immunologically competent, or developed, system by this time. It is possible that the supplement primed the immune system, starting with the innate system. This resulted in a more adaptive biased immune system in the supplemented birds by D42. Evidence for this includes the adaptive immune system pathway at D42 in the supplemented birds as well as the substantial changes in TLR signaling at D14.

TABLE 1

A) D14

| Reactome Pathway | Proteins | Background | FDR |
|---|---|---|---|
| Immune System | 122 | 1925 | 6.05E−35 |
| Signaling by Receptor Tyrosine Kinases | 136 | 2605 | 1.88E−32 |
| Signal Transduction | 84 | 1012 | 7.99E−31 |
| Signaling by Interleukins | 68 | 654 | 9.75E−30 |
| Innate Immune System | 56 | 437 | 2.77E−28 |
| Disease | 56 | 439 | 2.86E−28 |
| Cytokine Signaling in Immune System | 35 | 151 | 1.15E−24 |
| Disease of signal transduction | 47 | 360 | 6.48E−24 |
| Disease | 71 | 1018 | 1.04E−21 |
| Toll-like Receptor 4 (TLR4) Cascade | 30 | 126 | 2.06E−21 |
| MAPK family signaling cascades | 37 | 273 | 3.74E−19 |
| MyD88:MAL(TIRAP) cascade initiated on plasma membrane | 25 | 94 | 9.173−19 |
| Toll-like Receptor 3 (TLR3) Cascade | 25 | 95 | 9.78E−19 |
| Toll-like Receptor 4 (TLR4) Cascade | 25 | 96 | 1.08E−18 |
| TRIF (TICAM1)-mediated TLR4 signaling | 25 | 96 | 1.08E−18 |
| MyD88 cascade initiated on plasma membrane | 24 | 84 | 1.08E−18 |
| Intracellular signaling by second messengers | 36 | 274 | 1.59E−18 |
| TAF6 mediated induction of NFkB and MAP kinases upon TLR | 24 | 91 | 3.283−18 |
| P13K/AKT Signaling in Cancer | 23 | 85 | 1.07E−17 |
| Fc epsilon receptor (FCERI) signaling | 26 | 126 | 1.56E−17 |

TABLE 1

| B) D42 | | | |
|---|---|---|---|
| Reactome Pathway | Pro-teins | Back-ground | FDR |
| Immune System | 115 | 1925 | 6.05E−35 |
| Signaling by Receptor Tyrosine Kinases | 58 | 437 | 8.58E−32 |
| Signal Transduction | 126 | 2605 | 1.13E−30 |
| Signaling by Interleukins | 53 | 439 | 2.93E−27 |
| Innate Immune System | 75 | 1012 | 6.87E27 |
| Disease | 73 | 1018 | 2.56E−25 |
| Cytokine Signaling in Immune System | 59 | 654 | 1.06E−24 |
| Diseases of signal transduction | 43 | 360 | 7.70E−22 |
| Intracellular signaling by second messengers | 37 | 274 | 2.76E−20 |
| Signaling by VEGF | 25 | 104 | 1.17E−18 |
| VEGFA-VEGFR2 Pathway | 24 | 95 | 2.39E−18 |
| Signaling by NRKs | 24 | 97 | 3.32E−18 |
| Axon guidance | 46 | 541 | 4.10E−18 |
| MAPK family signaling cascades | 33 | 273 | 7.93E−17 |
| Signaling by NTRK1 (TRKA) | 21 | 76 | 9.14E−17 |
| PIP3 activates AKT signaling | 31 | 242 | 1.76E−16 |
| Toll-like Receptor Cascades | 26 | 151 | 1.76E−16 |
| Adaptive Immune System | 49 | 733 | 1.74E−15 |
| FC epsilon receptor (FCERI) signaling | 23 | 126 | 4.58E−15 |
| Developmental Biology | 57 | 1023 | 6.71E−15 |

Table 1: Small intestine (Meckel's adjacent) Reactome Pathways. Statistically significantly differentially phosphorylated proteins from the small intestine at D14 and D42 were input into the STRING database to generate a list of enriched Reactome Pathways. Table 1 A) D14 shows the top 20 pathways from D14, Table 1 B) D42 shows the top twenty pathways from D42. Highlighted in italics are the unique pathways from each time point. Much of the unique signaling at D14 is related to innate immune signaling, while the signaling at D42 is related to growth and the adaptive immune system. "Proteins" is the number of proteins within the pathway differentially phosphorylated on the array, "Background" is the number of proteins within the pathway, and "FDR" is false discovery rate significance value of the pathway.

The same analysis as above, run on the liver samples shows that there were few unique signaling pathways between D14 and D42 (Table 2 A and B). Those that were unique were related to growth: "Signaling by VEGF" at D14 and "MAPK family signaling cascades at D42." Of the differences between the two time points of particular interest was that there were two innate immune signaling pathways related to TLR signaling in the top twenty list at D14 that were not present at D42. That does not mean that there was no innate immune signaling or TLR signaling at D42. Instead, this means that there was additional unique TLR signaling at D14. This may again point to a more robust immune stimulation by the algae early in grow out, possibly maturing the tissue at this early point.

TABLE 2

| A) D14 | | | |
|---|---|---|---|
| Reactome Pathway | Pro-teins | Back-ground | FDR |
| Immune System | 152 | 1925 | 4.53E−24 |
| Signaling by Receptor Tyrosine Kinases | 78 | 437 | 4.69E−44 |
| Signal Transduction | 168 | 2605 | 1.91E−43 |
| Cytokine Signaling by Immune system | 84 | 654 | 3.60E−38 |
| Innate Immune System | 101 | 1012 | 5.56E−38 |
| Signaling by Interleukins | 71 | 439 | 102E−37 |
| Disease | 94 | 1018 | 1.22E−32 |
| Disease of signal transduction | 60 | 360 | 3.12E−32 |
| Toll-like Receptor Cascades | 40 | 151 | 1.34E−27 |
| Intracellular signaling by second messengers | 46 | 274 | 1.7E−24 |
| Toll-like Receptor 4 (TLR4) Cascade | 34 | 126 | 1.25E−23 |
| Signaling by VEGF | 32 | 104 | 1.25E−23 |
| VEGFA-VEGFR2 Pathway | 31 | 95 | 1.42E−23 |
| Signaling by NTRKs | 31 | 97 | 2.23E−23 |
| Signaling by NTRK1 (TRKA) | 28 | 76 | 1.86E−22 |
| Toll-like Receptor 9 (TLR9) Cascade | 30 | 96 | 2.03E−22 |
| PIP3 activates AKT signaling | 41 | 242 | 4.643−22 |
| TRAF6 mediated induction of NFkB and MAPk | 29 | 91 | 6.76E−22 |
| MyD88:MAL(TIRAP) cascade initiated on plasma membrane | 29 | 94 | 1.24E−21 |
| PI3I/AKT Signaling in Cancer | 28 | 85 | 1.50E−21 |

TABLE 2

| B) D42 | | | |
|---|---|---|---|
| Reactome Pathway | Pro-teins | Back-ground | FDR |
| Signaling by Receptor Tyrosine Kinases | 63 | 437 | 6.25E−41 |
| Signal Transduction | 124 | 2605 | 9.10E−28 |
| Immune System | 102 | 1925 | 3.39E−33 |
| Diseases of signal transduction | 48 | 360 | 1.77E−29 |
| Signaling by Interleukins | 50 | 439 | 5.51E−28 |
| Disease | 69 | 1018 | 7.42E−27 |
| Intracellular signaling by second messenger | 41 | 274 | 7.62E−27 |
| Cytokine Signaling in Immune System | 56 | 654 | 5.24E−26 |
| Innate Immune System | 67 | 1012 | 1.39E−25 |
| VEGFA-VEGFR2 Pathway | 28 | 95 | 5.17E−25 |
| PIP3 activates AKT signaling | 36 | 242 | 1.62E−23 |
| PI3K/AKT Signaling in Cancer | 25 | 85 | 2.583−22 |
| Signaling by NTRKs | 25 | 97 | 3.81E−21 |
| Signaling by NTRK1 (TRKA) | 23 | 76 | 9.28E−21 |
| Negative regulation of the PI3K/AKT network | 24 | 92 | 1.98E−20 |
| Toll-like Receptor Cascades | 27 | 151 | 2.36E−19 |
| MAPK family signaling cascades | 33 | 273 | 4.31E−19 |
| Toll-like Receptor 4 (TLR4) Cascade | 25 | 126 | 7.14E−19 |
| TRAF6 mediated induction of NFkB | 22 | 91 | 3.76E−18 |
| Axon guidance | 42 | 541 | 5.95E−18 |

Table 2: Liver Reactome Pathways. Statistically significantly differentially phosphorylated proteins from the liver at D14 and D42 were input into the STRING database to generate a list of enriched Reactome Pathways. Table 2 A) D14 shows the top twenty pathways from D14, Table 2 B) D42 shows the top twenty pathways from D42. Highlighted in italics are the unique pathways from each time point. Unique to D14 (Table 2 A) D14) is a mix of growth and innate immune signaling. In Table 2 B) D42 growth represents a unique characteristic. This may indicate priming and growth early while later the supplement enhances growth related signaling.

The differential responses in the muscle were functionally quite different between the D14 and D42 pathways (Table 3 A and B). At D42 in the muscle there was a mix of pro-growth (MAPK, AKT) signaling and innate immune signaling (TLR4 and 9) (Table 3B). At D14 there was TRAF6 mediated innate immune signaling but the other two unique pathways were related to NTRK signaling (Table 3A). NTRKs are neuronal related signaling receptors that leads to cell differentiation and MAPK related growth. There function has been shown to be associated with muscle-bone formation, cell growth and immune response to the alpha-toxin of *Clostridium perfringens*. These effects of the algae on the muscle have many intriguing possibilities such as improved muscle/bone development, further growth of muscle or immune priming, all found early and in the muscle compared to later in grow-out.

TABLE 3

A) D14

| Reactome Pathway | Proteins | Background | FDR |
|---|---|---|---|
| Signal Transduction | 130 | 2605 | 1.65E−32 |
| Immune System | 111 | 1925 | 4.34E−32 |
| Signaling by Receptor Tyrosine Kinases | 57 | 437 | 7.32E−31 |
| Innate Immune System | 78 | 1012 | 6.60E−29 |
| Diseases of signal transduction | 49 | 360 | 3.81E−27 |
| Cytokine Signaling in Immune system | 61 | 654 | 3.87E−26 |
| Signaling by Interleukins | 51 | 439 | 1.50E−25 |
| Disease | 71 | 1018 | 8.23E−24 |
| Signaling by NTRKs | 27 | 97 | 1.49E−21 |
| Toll-like Receptor Cascades | 31 | 151 | 1.60E−21 |
| Signaling by NTRK1 (TRKA) | 25 | 76 | 1.82E−21 |
| MAPK family signaling cascades | 36 | 273 | 1.94E−19 |
| TRAF6 mediated induction of NFkB and MAP kinases | 24 | 91 | 9.58E−19 |
| MyD88:MAL(TIRAP) cascade initiated on plasma membrane | 24 | 94 | 1.49E−18 |
| VEGF-VEGFR2 Pathway | 24 | 95 | 1.63E−18 |
| Toll-like Receptor 4 (TLR4) Cascade | 26 | 126 | 2.77E−18 |
| MyD88 cascade initiated on plasma membrane | 22 | 84 | 2.48E−18 |
| PI3KI/AKT Signaling on Cancer | 22 | 85 | 2.74E−17 |
| Intracellular signaling by second messengers | 33 | 274 | 5.14E−17 |
| Toll-like Receptor 3 (TLR3) Cascade | 22 | 95 | 1.96E−16 |

TABLE 3

B) D42

| Reactome Pathway | Proteins | Background | FDR |
|---|---|---|---|
| Immune System | 134 | 1925 | 6.30E−46 |
| Innate Immune System | 91 | 1012 | 5.36E−37 |
| Signaling by Receptor Tyrosine Kinases | 62 | 437 | 3.31E−34 |
| Signal Transduction | 136 | 2605 | 6.38D−34 |
| Signaling by Interleukins | 58 | 439 | 1.60E−30 |
| Disease of signal transduction | 52 | 360 | 7.08E−29 |
| Cytokine Signaling in Immune system | 66 | 654 | 7.21E−29 |
| Disease | 80 | 1018 | 1.01E−28 |
| VEGFA-VEGFR2 Pathway | 28 | 95 | 2.95E−22 |
| MAPK family signaling cascades | 40 | 273 | 3.23E−22 |
| Toll-like Receptor Cascades | 32 | 151 | 7.21E−22 |
| Intracellular signaling by second messengers | 37 | 274 | 1.78E−19 |
| PI3KI/AKT Signaling on Cancer | 24 | 85 | 9.25E−19 |
| Toll-like Receptor 4 (TLR4) Cascade | 27 | 126 | 1.52E−18 |
| Toll-like Receptor 3 (TLR3) Cascade | 24 | 95 | 7.37E−18 |
| TRIF(TICAM1)-mediated TLR4 signaling | 24 | 96 | 8.54E−18 |
| MAPK1/MAPK3 signaling | 32 | 234 | 5.09E−17 |
| MyD88:MAL(TIRAP) cascade initiated on plasma membrane | 23 | 94 | 6.42E−17 |
| Toll-like Receptor 9 (TLR9) Cascade | 23 | 96 | 8.72E−17 |
| PIP3 activates AKT signaling | 32 | 242 | 9.27E−17 |

Table 3: Muscle Reactome Pathways. Statistically significantly differentially phosphorylated proteins from the muscle at D14 and D42 were input into the STRING database to generate a list of enriched Reactome Pathways. Table 3 A) D14 shows the top twenty pathways from D14 while Table 3 B) D42 shows the top twenty pathways from D42. Highlighted in italics are the unique pathways from each time point. NTRK signaling is shown in the muscle at D14 in Table 3 A) D14. At D42 in Table 3 B) D42 there is a mix of immune and growth related signaling. "Proteins" is the number of proteins within the pathway differentially phosphorylated on the array, "Background" is the number of proteins within the pathway, "FDR" is false discovery rate significance value of the pathway.

In the ceca, there is a limited number of unique signaling pathways between D14 and D42. While Signaling by NTRKs was unique to D14, Signaling by NTRK1 shows up at both D14 and D42, and this pathway is likely associated with simple cell growth responses, possibly immune related. Signaling by VEGF is also unique at D14 but signaling by VEGFA-VEGFR2 Pathway is present at D42 and is a subset of this larger pathway group, again related to cellular growth signals. At D42, Akt signaling and TLR signaling through MyD88 are unique and represent a mix of growth and immune signaling not present at D42. However, overall it does not appear that the algae results in significant changes between D14 and D42 in the ceca, as compared to the other tissues.

TABLE 4

A) D14

| Reactome Pathway | Proteins | Background | FDR |
|---|---|---|---|
| Immune System | 154 | 1925 | 9.14E−47 |
| Signal Transduction | 176 | 2605 | 1.35E−45 |
| Signaling by Receptor Tyrosine Kinases | 75 | 437 | 5.60E−40 |
| Innate Immune System | 104 | 1012 | 1.99E−38 |
| Diseases of signal transduction | 61 | 360 | 6.74E−32 |
| Cytokine Signaling in Immune system | 7 | 654 | 6.74E−32 |
| Signaling by Interleukins | 65 | 439 | 3.53E−31 |
| Disease | 94 | 1018 | 3.53E−31 |
| Toll-like Receptor Cascades | 42 | 151 | 3.92E−31 |
| MAPK family signaling cascades | 48 | 273 | 4.96E−29 |
| Toll-like Receptor 4 (TLR4) Cascade | 35 | 126 | 1.34E−25 |
| Intracellular signaling by second messengers | 46 | 274 | 4.63E−24 |
| Signaling by NTRKs | 30 | 97 | 8.44E−24 |
| TRAF6 mediated induction of NFkB and MAP kinases | 29 | 91 | 1.08E−21 |
| Signaling by VEGF | 30 | 104 | 2.80E−21 |
| MyD88:MAL(TIRAP) cascade initiated on plasma membrane | 29 | 94 | 4.48E−21 |
| Toll-Like Receptor 3 (TLR3) Cascade | 29 | 95 | 4.65E−21 |
| PI3KI/AKT Signaling on Cancer | 28 | 85 | 5.35E−21 |
| VEGFA-VEGFR2 Pathway | 29 | 95 | 5.35E−21 |
| Signaling by NTRK1 (TRKA) | 27 | 76 | 5.36E−21 |

TABLE 4

B) D42

| Reactome Pathway | Proteins | Background | FDR |
|---|---|---|---|
| Immune System | 113 | 1925 | 1.28E−36 |
| Signaling by Receptor Tyrosine Kinases | 60 | 43 | 1.98E−35 |
| Signal Transduction | 125 | 2605 | 2.18E−33 |
| Innate Immune System | 78 | 1012 | 3.48E−31 |
| Signaling by Interleukins | 53 | 439 | 8.52E−29 |
| Cytokine Signaling in Immune System | 62 | 654 | 8.84E−29 |
| Diseases of single transduction | 46 | 360 | 8.65E−26 |
| Intracellular signaling by second messengers | 39 | 274 | 3.36E−23 |
| Disease | 66 | 1018 | 3.89E−22 |
| Signaling by NRK1 (TRKA) | 24 | 76 | 6.78E−21 |
| Toll-like Receptor Cascades | 29 | 151 | 2.99E−20 |
| VEGFA-VEGFR2 Pathway | 25 | 95 | 3.05E−20 |
| PI3K/AKT Signaling in Cancer | 24 | 85 | 4.82E−20 |

TABLE 4-continued

| B) D42 | | | |
|---|---|---|---|
| Reactome Pathway | Proteins | Background | FDR |
| Toll-like Receptor 4 (TLR4) Cascade | 27 | 126 | 5.63E−20 |
| PIP3 activates AKT signaling | 33 | 242 | 3.37E−19 |
| MyD88 cascade initiated on plasma membrane | 23 | 84 | 4.90E−19 |
| MAPK family signaling cascades | 34 | 273 | 8.44E−19 |
| TRAF6 mediated induction of NFkB and MAP kinases upon TLR7/8 or 9 | 23 | 91 | 1.75E−18 |
| MyD88:MAL(TIRAP) cascade initiated on plasma membrane | 23 | 94 | 2.89E−18 |
| Toll-like Receptor 3 (TL3) Cascade | 23 | 95 | 3.29E−18 |

Table 4: Ceca Reactome Pathways. Statistically significantly differentially phosphorylated proteins from the ceca at D14 and D42 were input into the STRING database to generate a list of enriched Reactome Pathways. Table 4 A) D14 shows the top twenty pathways from D14 while Table 4 B) D42 shows the top twenty pathways from D42. Highlighted in italics are the unique pathways from each time point. "Proteins" is the number of proteins within the pathway differentially phosphorylated on the array, "Background" is the number of proteins within the pathway, "FDR" is false discovery rate significance value of the pathway.

While not showing up in the top twenty of Reactome Pathways, in all tissues and time points there was a broad pathway called "Metabolism" that showed significant changes between algae supplementation and the control. The significantly differentially phosphorylated proteins within the Metabolism pathway were compared between D14 and D42 for each tissue. Those proteins that are unique to each time point were uploaded into STRING. Within the resulting protein interaction groups (FIGS. 5A, 5B, 6A, 6B, 7A, 7B, and 8) there were certain macronutrient metabolic processes that were enriched. The fact that the unique proteins generated overwhelmingly contiguous protein-protein interaction networks indicates that these proteins are part of an interacting metabolic process and are not just disparate phosphorylation changes.

Figure 5A:
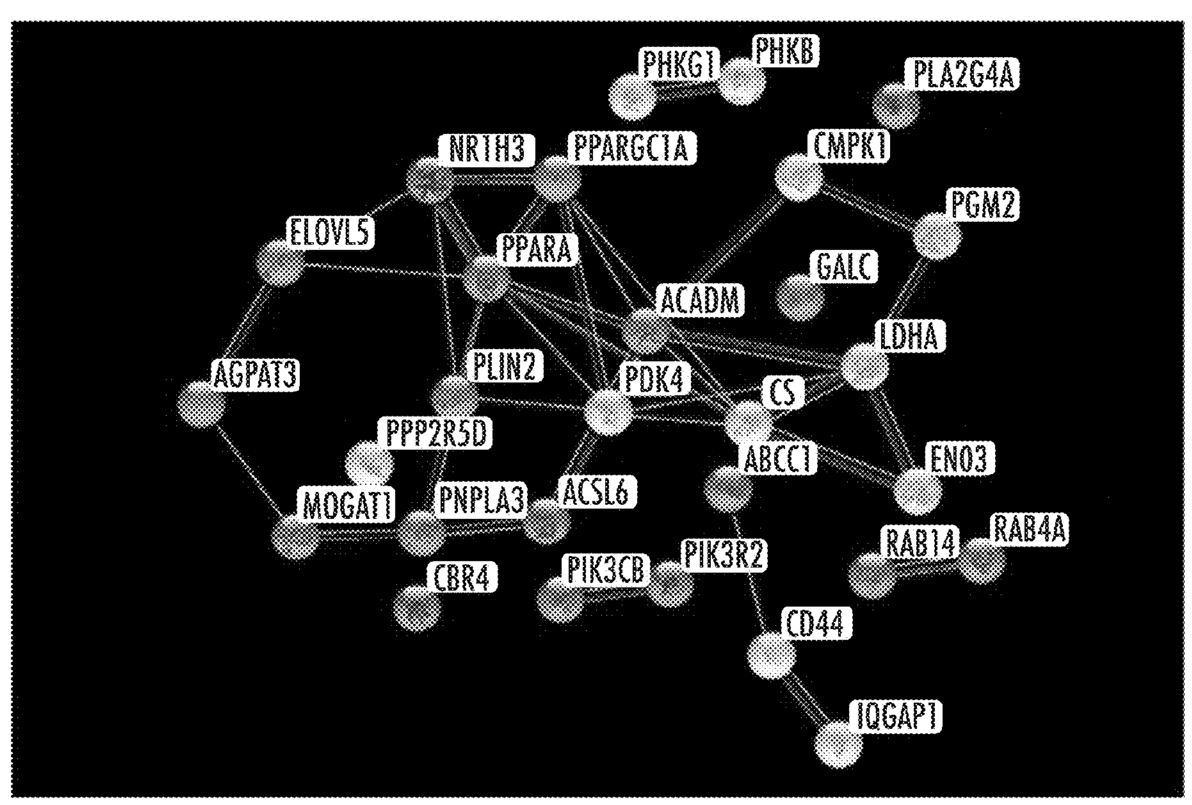
FIG. 5A illustrates "Metabolism" Reactome Pathway members in the small Intestine (Meckel's adjacent) at Day 14.
Figure 5B:
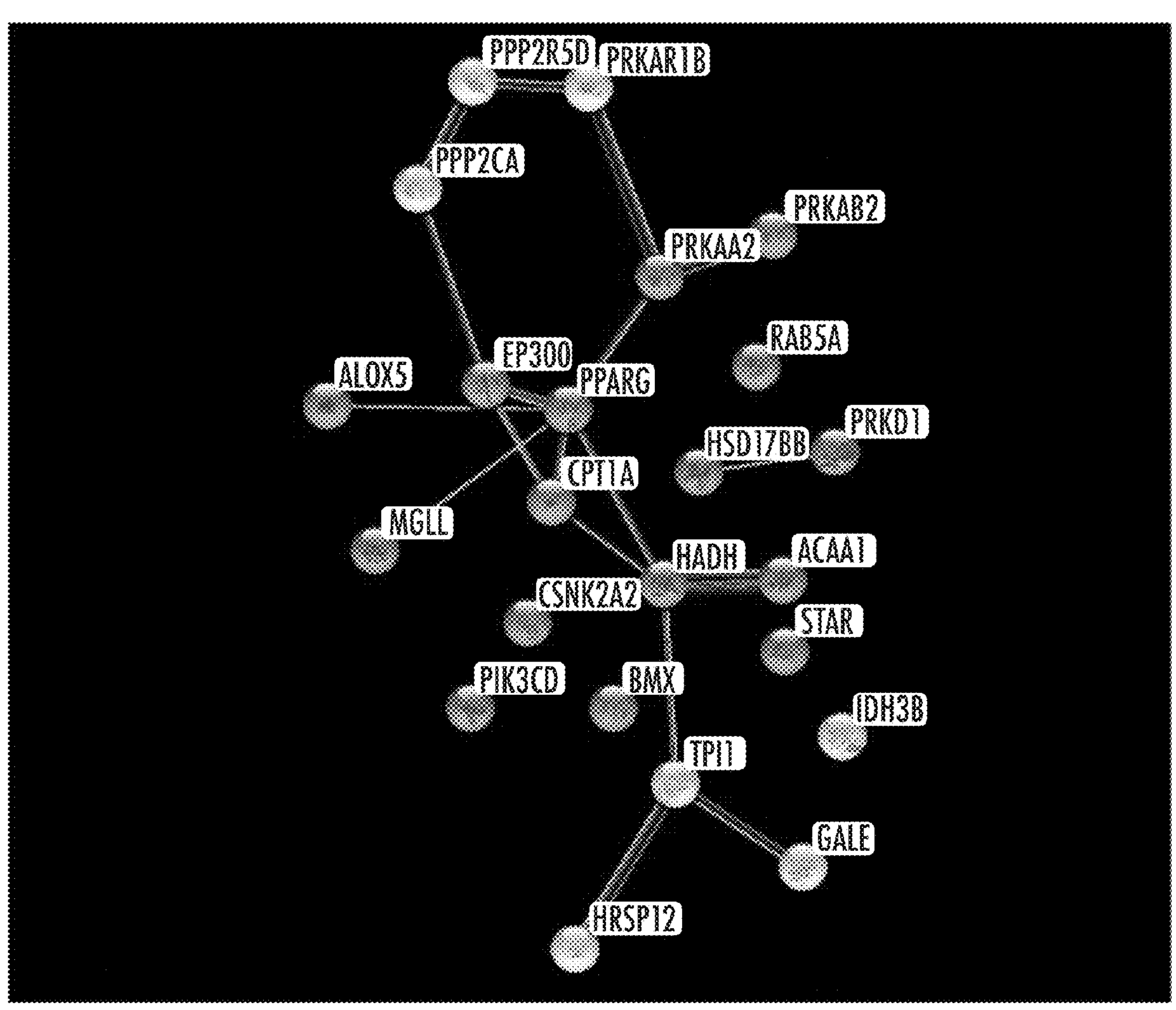
FIG. 5B illustrates "Metabolism" Reactome Pathway members in the small Intestine (Meckel's adjacent) at Day 42.

In the small intestine, at both D14 and D42, within the "Metabolism" pathway, the unique protein interaction groups were enriched for "Metabolism of Lipids" (FIGS. 5A and 5B). Thus, despite differences in response to the algae at the two different ages of birds, a major effect was to alter the metabolism of lipids in the gut.

FIGS. 5A and 5B illustrate unique "Metabolism" Reactome Pathway members in the small intestine (Meckel's adjacent). Proteins that were unique to each time point within the "Metabolism" Reactome pathway were input into STRING to generate protein-protein interaction groups. Red proteins are members of the "Metabolism of Lipids" pathway for both D14 (FIG. 5A) and D42 (FIG. 5B).

Figure 6A:
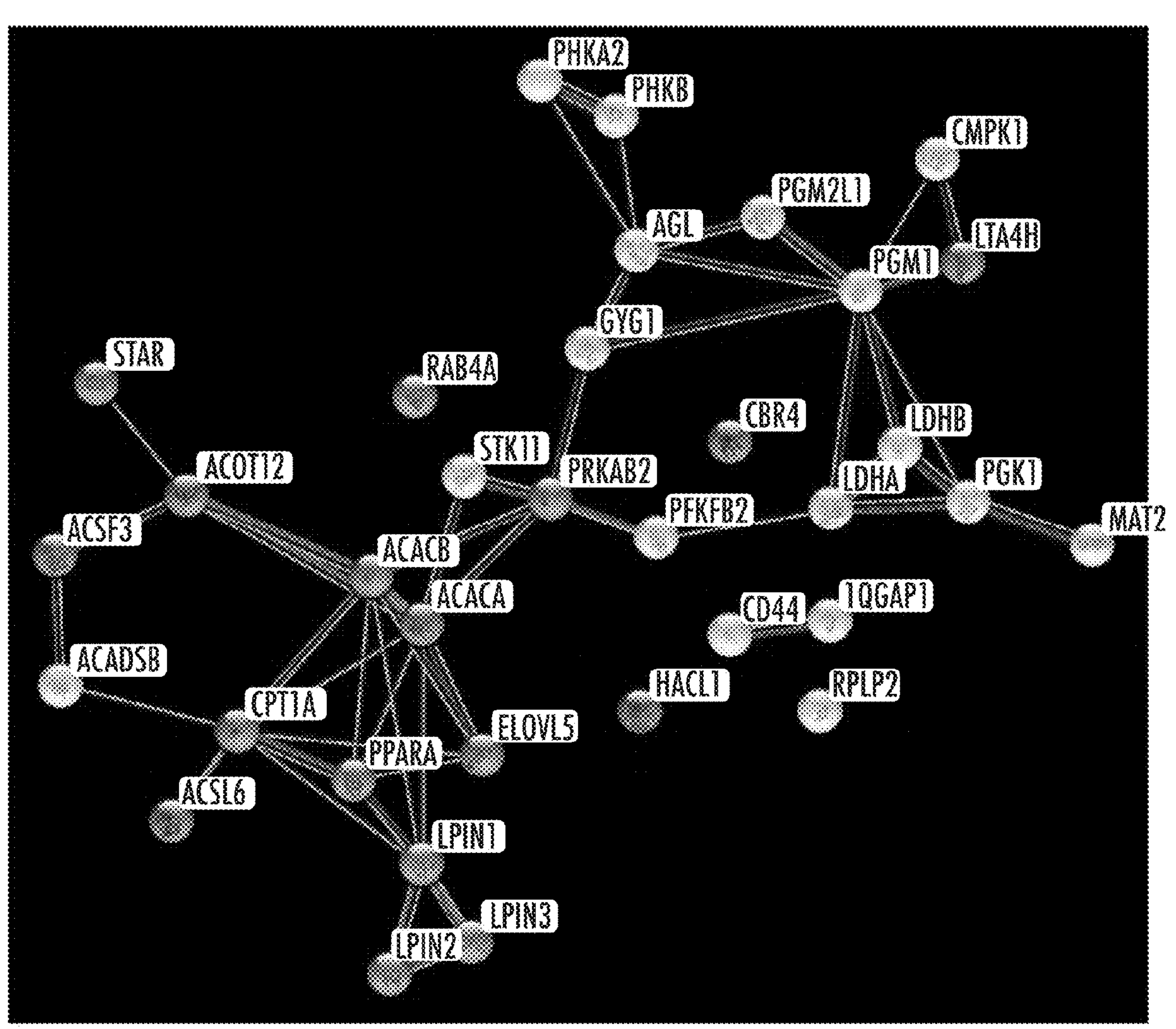
FIG. 6A illustrates "Metabolism" Reactome Pathway members in the liver at Day 14.
Figure 6B:
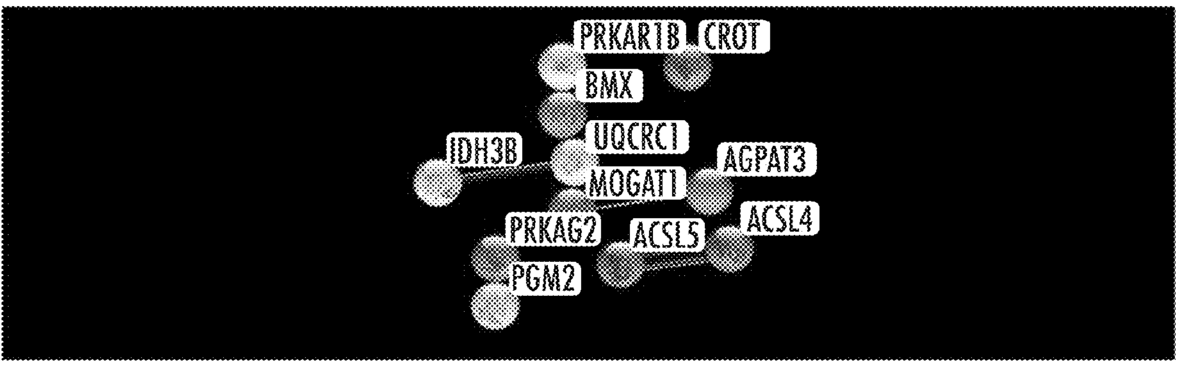
FIG. 6B illustrates "Metabolism" Reactome Pathway members in the liver at Day 42.

FIGS. 6A and 6B illustrate unique "Metabolism" Reactome Pathway members in the liver. In the liver, at both D14 and D42, within the "Metabolism" pathway, the unique protein interaction groups were enriched for "Metabolism of lipids" and "Fatty acid metabolism." Thus, despite differences in response to the algae at the two different ages, a major effect was to alter the metabolism of fats in the gut. As the liver is a major processor of lipids and fats, and lipid metabolism is altered in the gut. This result is consistent with the data described above.

Proteins that were unique to each time point within the "Metabolism" Reactome pathway were input into STRING to generate protein-protein interaction groups. Red proteins are members of the "Metabolism of Lipids" pathway and purple proteins are members of the "Fatty acid metabolism" pathway for both D14 (FIG. 6A) and D42 (FIG. 6B).

Figure 7A:
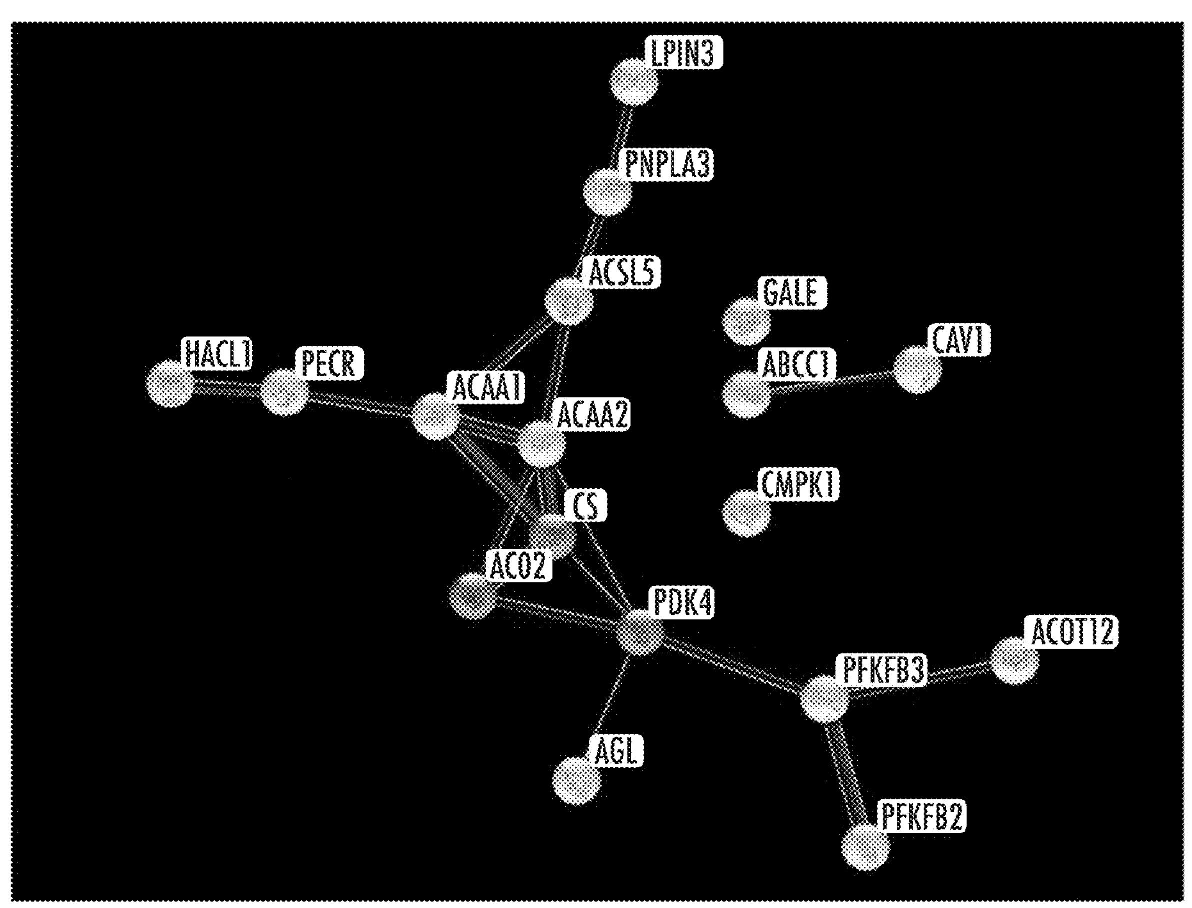
FIG. 7A illustrates "Metabolism" Reactome Pathway members in the muscle at Day 14.
Figure 7B:
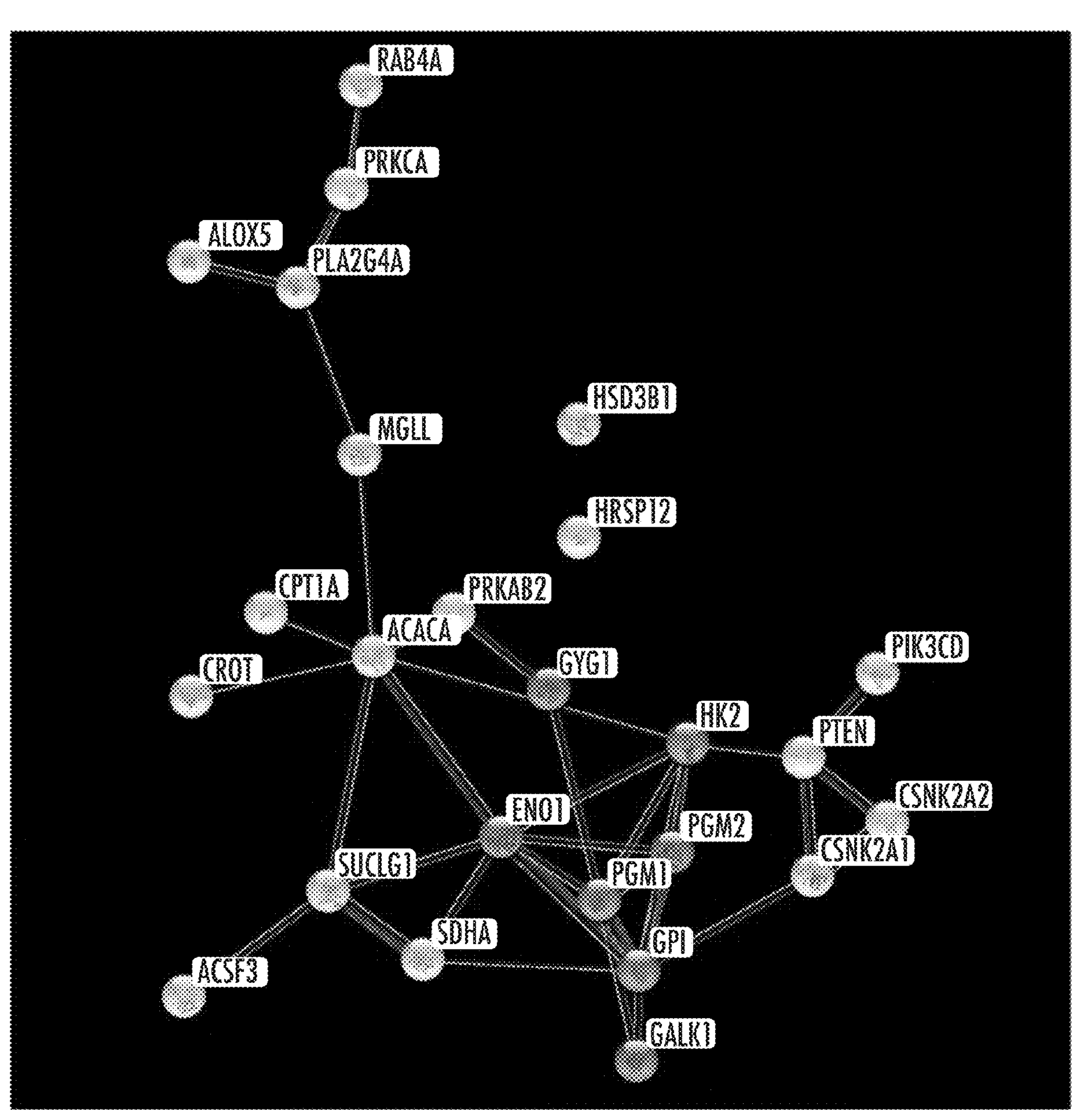
FIG. 7B illustrates "Metabolism" Reactome Pathway members in the muscle at Day 42.

FIGS. 7A and 7B illustrate unique "Metabolism" Reactome Pathway members in the muscle. In the muscle, at both D14 and D42, within the "Metabolism" pathway, the unique protein interaction groups were enriched for "Pyruvate metabolism and TCA cycle" and "Metabolism of carbohydrates", respectively. Thus, a major effect of the algae supplementation was to alter the TCA cycle early and the metabolism of carbohydrates late. As the muscle is a major consumer of glucose, this is consistent with increased muscle deposition and thus growth. This may even signal a greater feed conversion ratio potential.

Proteins that were unique to each time point within the "Metabolism" Reactome pathway were input into STRING to generate protein-protein interaction groups. Red proteins are members of the "Pyruvate metabolism and TCA cycle" pathway at D14 (FIG. 7A) and "Metabolism of carbohydrates" at D42 (FIG. 7B).

In the ceca, at D14, within the "Metabolism" pathway, the unique protein interaction groups were enriched for "Metabolism of Lipids." Again a major effect of the algae supplementation can be observed to alter lipid metabolism early. There were no significant protein interaction groups or enrichment of function in the ceca at D42. Thus, most of the unique changes occurred early within metabolism. Consistent with the small intestinal tissue metabolic data, lipid metabolism was altered in the gut by the algae.

Figure 8:
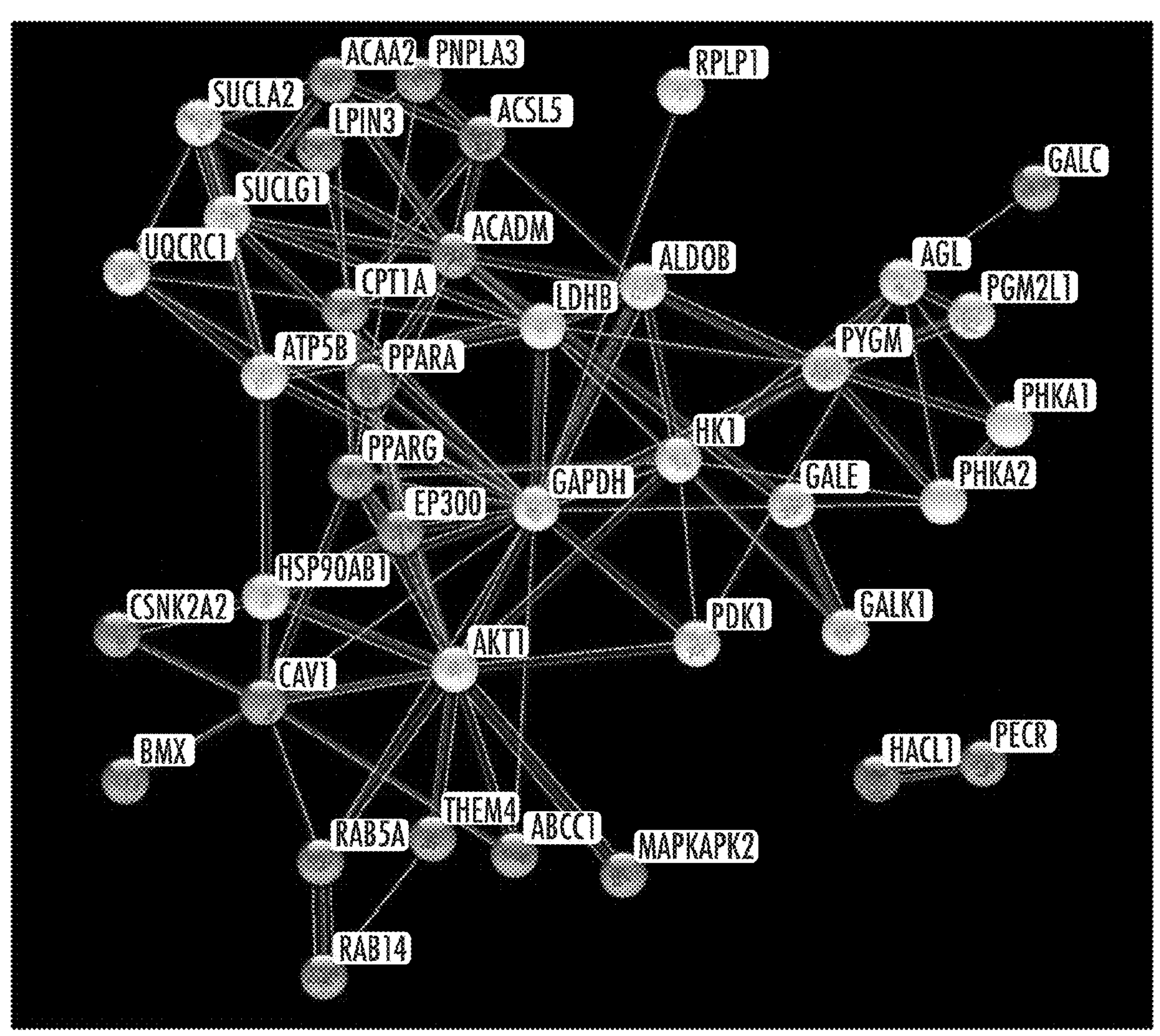
FIG. 8 illustrates "Metabolism" Reactome Pathway members in the ceca.

FIG. 8 illustrates unique "Metabolism" Reactome Pathway members in the ceca. Proteins that were unique to each time point within the "Metabolism" Reactome pathway were input into STRING to generate protein-protein interaction groups. Red proteins are members of the "Metabolism of Lipids" pathway at D14. D42 did not display any significant protein interaction groups and thus is not shown.

In all tissues and time points "Innate Immune System" was present in the top twenty significant Reactome Pathways, indicating this immune response was significantly changed between algae supplementation and the control (Tables 1-4). The significantly differentially phosphorylated proteins within the Innate Immune System pathway were compared between D14 and D42 for each tissue. Those proteins that were unique to the time point were uploaded into STRING.

Within the resulting protein interaction groups (FIGS. 9A, 9B, 10A, 10B, 11A, 11B, and 12), Toll-like signaling was enriched in all cases with the exception of ceca and liver at D42. The fact that this pathway was not present in these two tissues' unique responses at D42 is further evidence that the main effects of the algae supplementation occur early in grow-out.

Figure 9A:
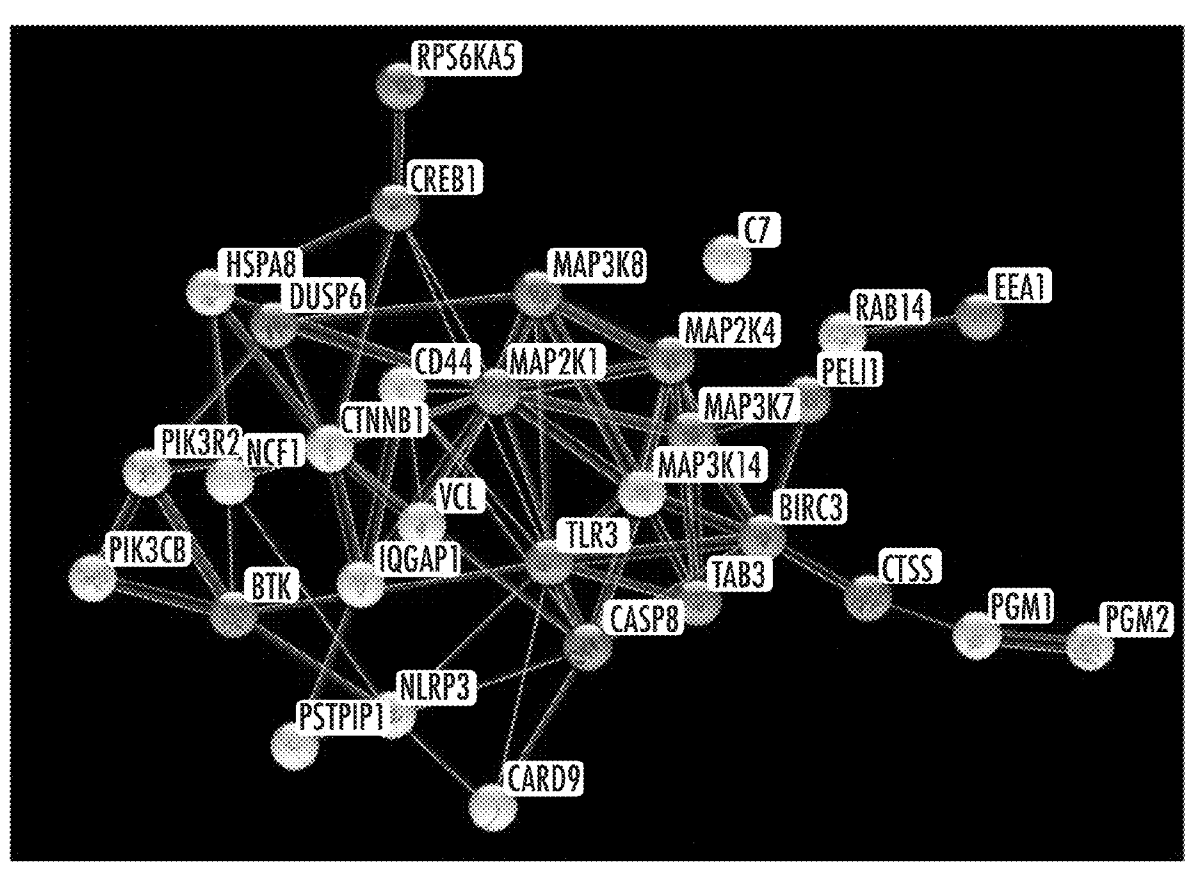
FIG. 9A illustrates "Innate Immune System" Reactome Pathway members in the small Intestine (Meckel's adjacent) at Day 14.
Figure 9B:
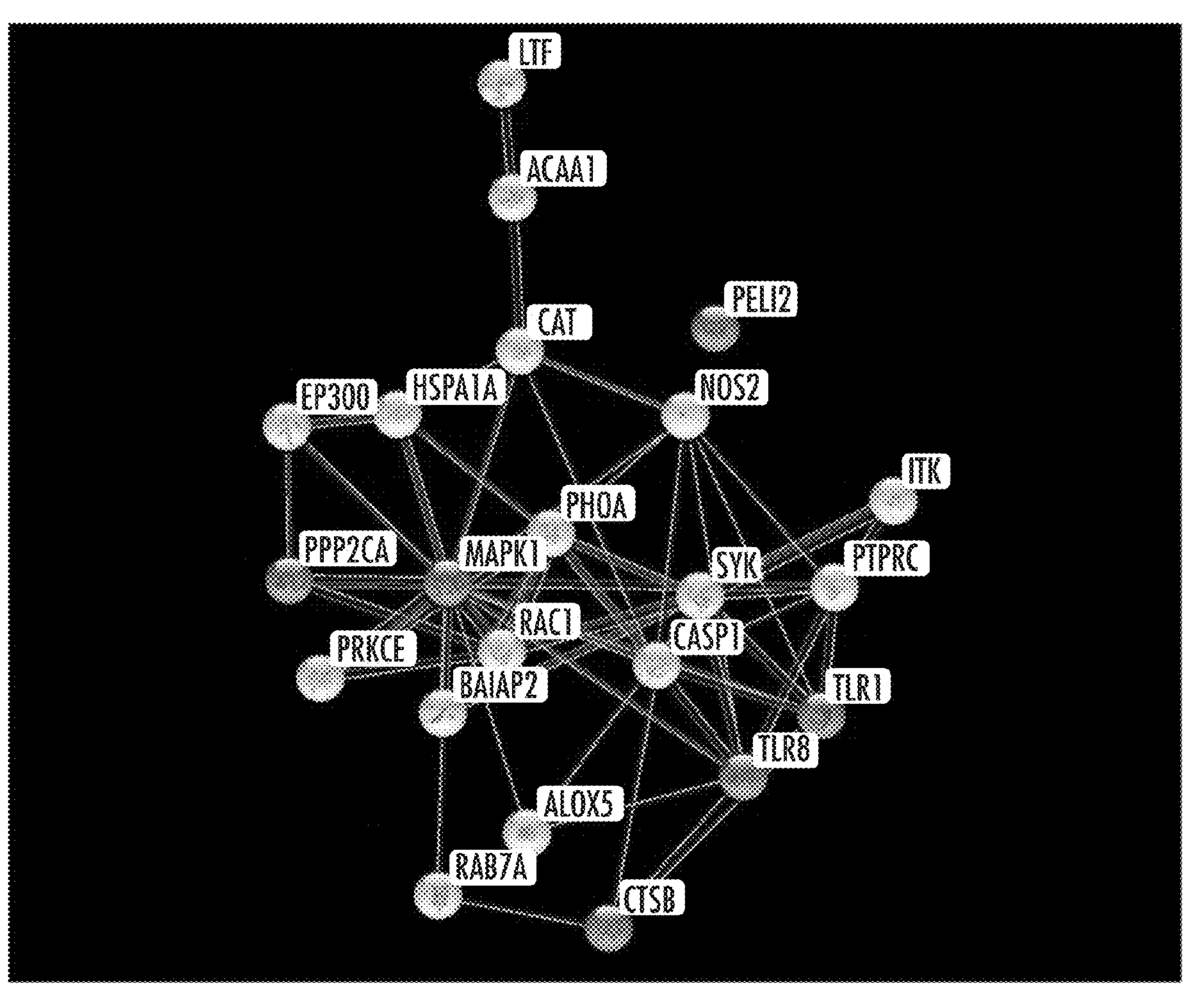
FIG. 9B illustrates "Innate Immune System" Reactome Pathway members in the small Intestine (Meckel's adjacent) at Day 42.

FIGS. 9A and 9B illustrate unique "Innate Immune System" Reactome Pathway members in the small intestine (Meckel's adjacent). Proteins that were unique to each time point within the "Innate Immune System" Reactome pathway were input into STRING to generate protein-protein interaction groups. Red proteins are members of the "Toll-like receptor cascades" pathway for both D14 (FIG. 9A) and D42 (FIG. 9B).

Figure 10A:
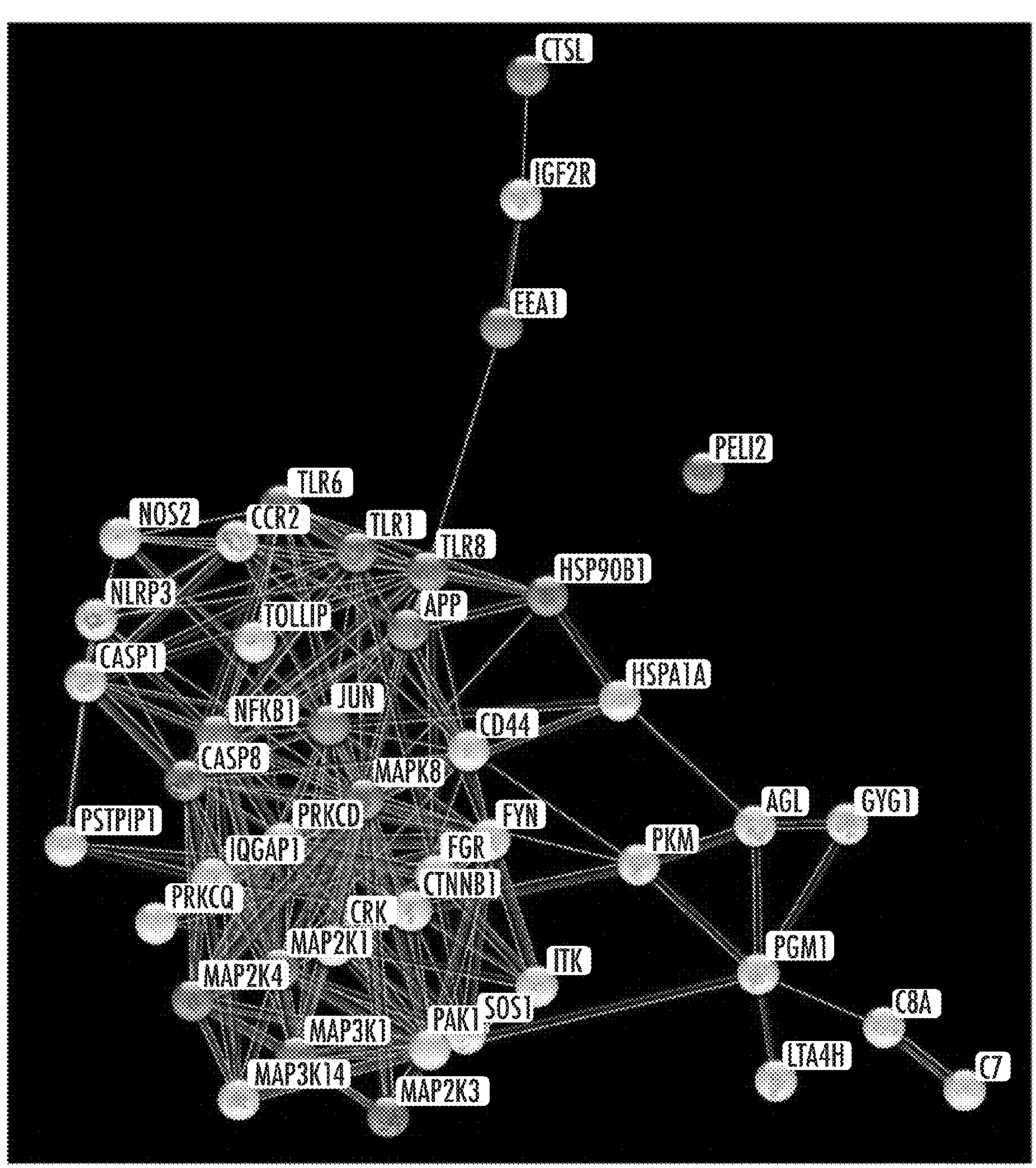
FIG. 10A illustrates "Innate Immune System" Reactome Pathway members in the liver at Day 14.
Figure 10B:
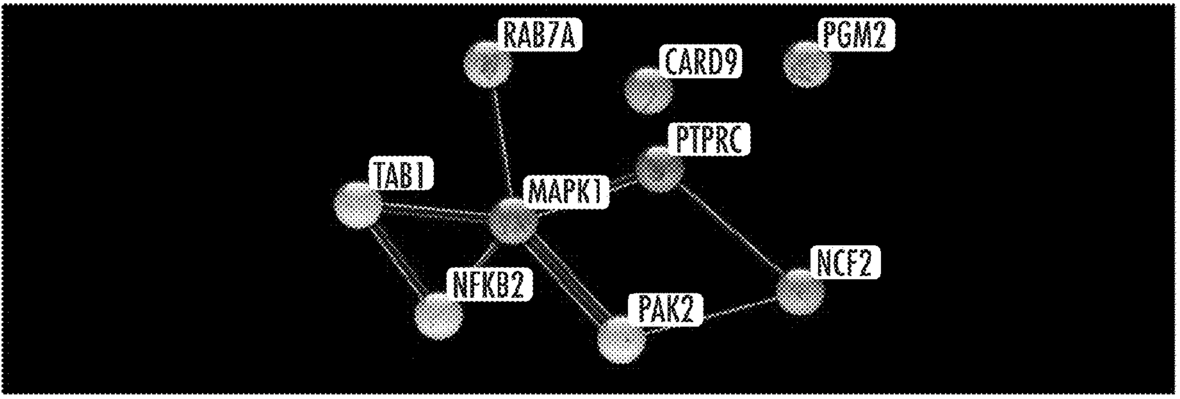
FIG. 10B illustrates "Innate Immune System" Reactome Pathway members in the liver at Day 42.

FIGS. 10A and 10B illustrates unique "Innate Immune System" Reactome Pathway members in the liver. Proteins that were unique to each time point within the "Innate Immune System" Reactome pathway were input into STRING to generate protein-protein interaction groups. Red proteins are members of the "Toll-like receptor cascades" pathway for D14 (FIG. 10A). There was no "Toll-like receptor cascades" pathway found at in D42 (FIG. 10B).

Figure 11A:
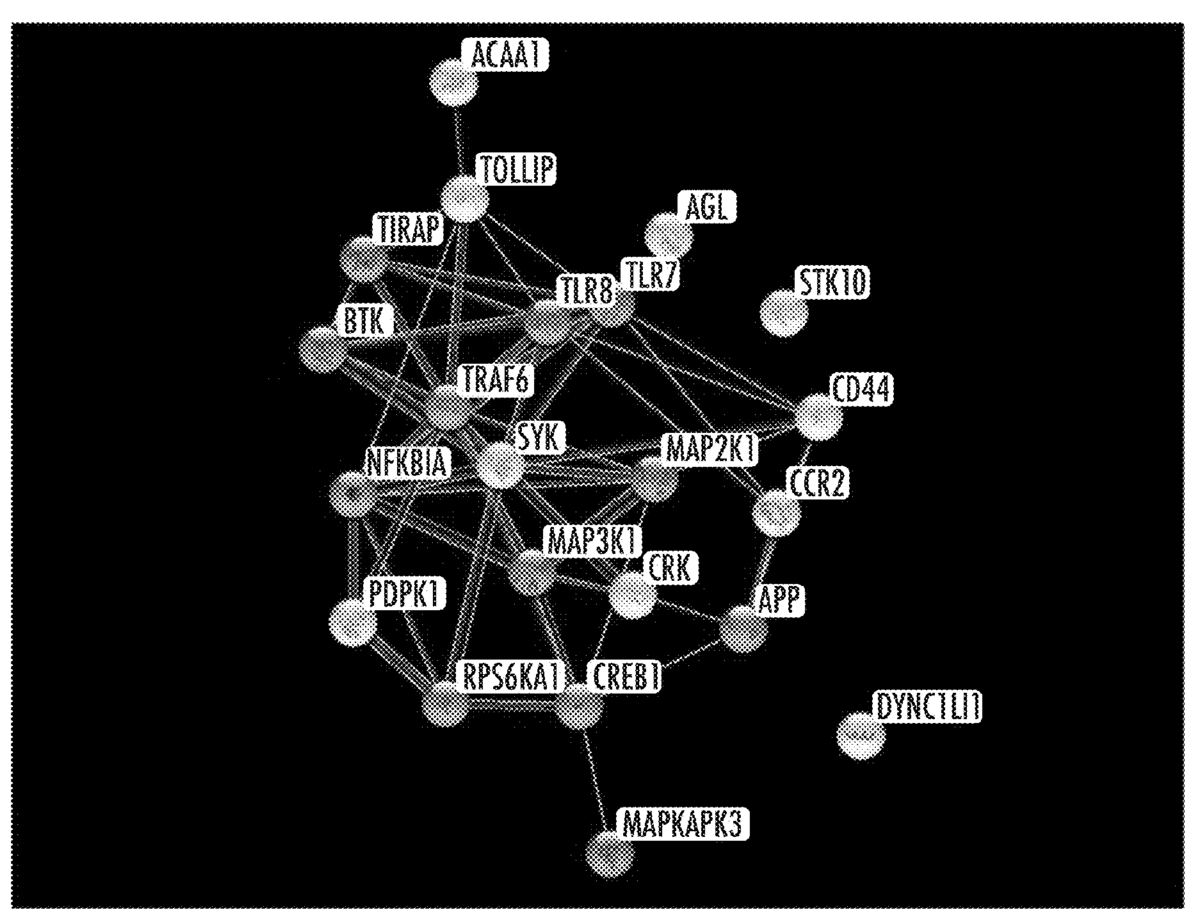
FIG. 11A illustrates "Innate Immune System" Reactome Pathway members in the muscle at Day 14.
Figure 11B:
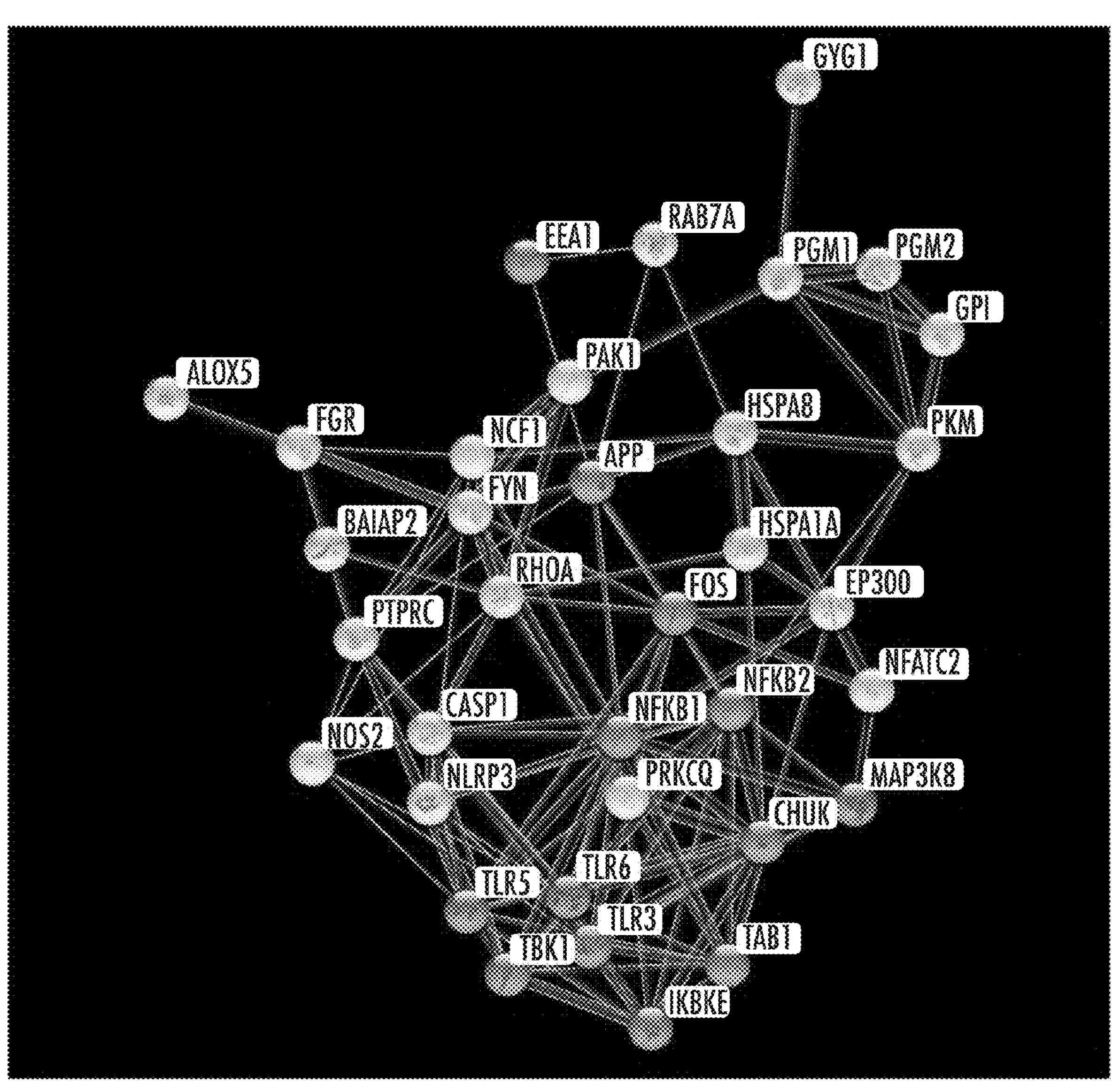
FIG. 11B illustrates "Innate Immune System" Reactome Pathway members in the muscle at Day 42.

FIGS. 11A and 11B illustrate unique "Innate Immune System" Reactome Pathway members in the muscle. Proteins that were unique to each time point within the "Innate Immune System" Reactome pathway were input into STRING to generate protein-protein interaction groups. Red proteins are members of the "Toll-like receptor cascades" pathway for D14 (FIG. 11A). No "Toll-like receptor cascades" pathway was found at in D42 (FIG. 11B).

Figure 12:
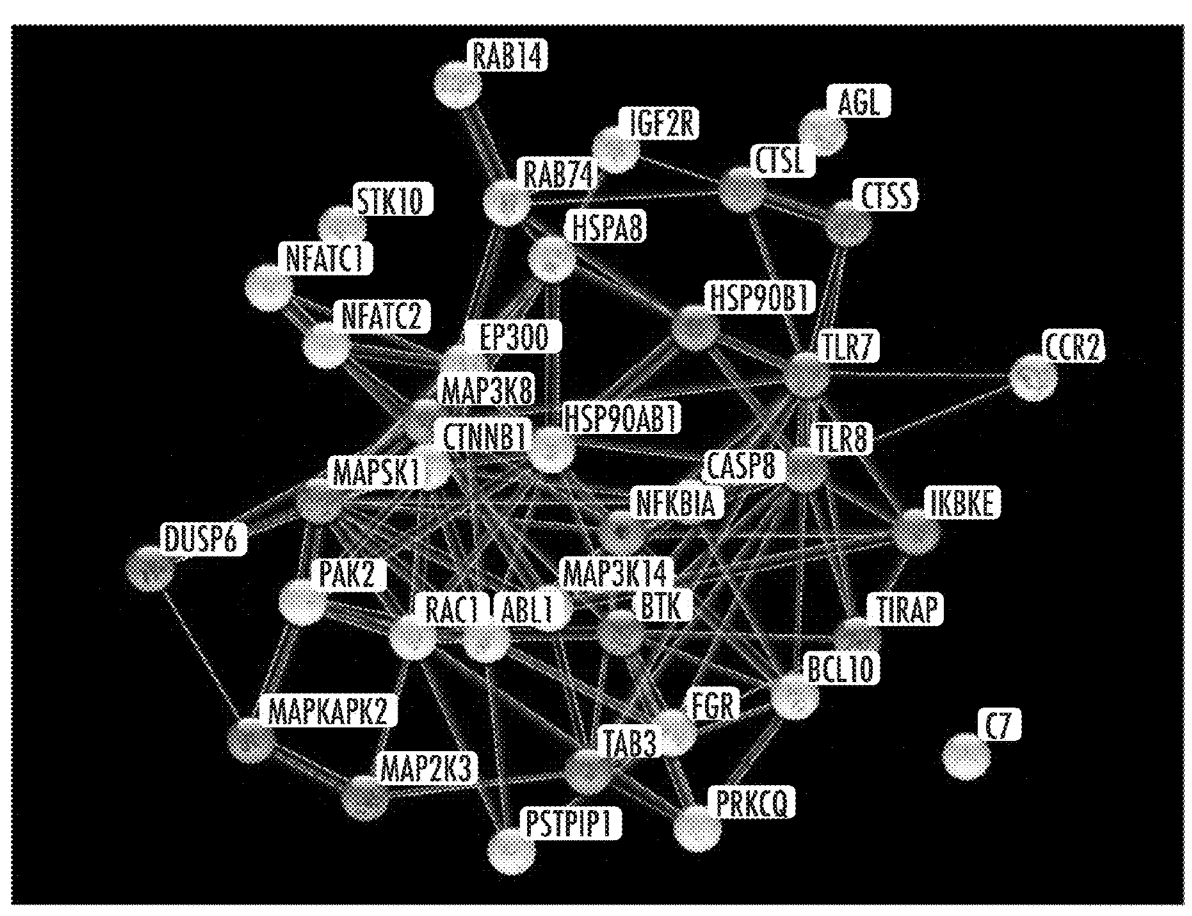
FIG. 12 illustrates "Innate Immune System" Reactome Pathway members in the ceca.

FIG. 12 illustrates unique "Innate Immune System" Reactome Pathway members in the ceca. Proteins that were unique to each time point within the "Innate Immune System" Reactome pathway were input into STRING to generate protein-protein interaction groups. Red proteins are members of the "Toll-like receptor cascades" pathway for D14 (A). No protein interaction group could be generated for D42.

Results

In general, kinomics analysis of poultry tissue from birds provided a feed mixture that included the disclosed compound demonstrated a significant maturing of innate immune pathways at Day 14 when compared with sacrificed birds fed a conventional feed mixture. Also, in general, kinomics analysis of poultry tissue from birds provided a feed mixture that included the disclosed compound demonstrated significant enhancement of adaptive immune pathways at Day 42.

Ultimately, kinomic analysis of the broiler tissues from both groups of chickens fed the treatment compound according to the regimen set forth above as well as those not fed the treatment compound verified that the treated chickens demonstrated an increase in adaptive immune response indicating a more immunologically competent or developed immune system. Significantly, the kinomic analysis indicated that treatment with the disclosed compound resulted in a more adaptive-biased immune system in the supplemented birds and further demonstrated an alteration of immunometabolism in gut, liver, and muscle tissue by priming the animal for a more rapid and robust immune response compared to birds receiving a standard, unfortified diet.

One indicator of the change in status was the detection of substantial changes in TLR signaling at Day 14. Evidence for this finding further includes modulating the adaptive immune system pathway identified at Day 42 in the feed-supplemented birds. Advantageously, studies showed that the identified immunomodulatory adaptation does not come at the cost of impaired growth and development, rather facilitates metabolic efficiency in the latter part of life. By following the method and treatment of the disclosed inventive concept, a more rapid, adaptive immune response in animals is possible, compared to a response usually seen in a 42 day-old bird.

We claim:

1. Feed for poultry including a non-antibiotic composition comprising a lipopolysaccharide derived from Gram-negative bacterium selected from the group consisting of *Variovorax paradoxus* and *Rhodobacter sphaeroides*, where the non-antibiotic composition is included in the feed in an amount from about 0.5 lbs. composition per U.S. ton of finished feed to about 5.0 lbs. composition per U.S. ton of finished feed.

2. The feed for use according to claim 1, wherein the non-antibiotic composition is fed to the poultry in an amount from about 1.0 lbs. composition per U.S. ton of finished feed to about 5.0 lbs. composition per U.S. ton of finished feed.

3. The feed for use according to claim 2, wherein the non-antibiotic composition is fed to the poultry in an amount from about 3.0 lbs. composition per U.S. ton of finished feed to about 0.2 lbs. composition per U.S. ton of finished feed.

* * * * *